US012758547B2

(12) United States Patent
Ahmed et al.

(10) Patent No.: US 12,758,547 B2
(45) Date of Patent: Oct. 13, 2026

(54) LONG ACTING INJECTABLE FORMULATIONS

(71) Applicant: Abon Pharmaceuticals, LLC, Northvale, NJ (US)

(72) Inventors: Salah U. Ahmed, New City, NY (US); Yanming Zu, Tenafly, NJ (US); Jason LePree, Demarest, NJ (US); Hetalben Prajapati, New Milford, NJ (US); Tahseen A. Chowdhury, Washington-Township, NJ (US)

(73) Assignee: Abon Pharmaceuticals, LLC, Northvale, NJ (US)

( * ) Notice: Subject to any disclaimer, the term of this patent is extended or adjusted under 35 U.S.C. 154(b) by 0 days.

(21) Appl. No.: 18/165,798

(22) Filed: May 2, 2023

(65) Prior Publication Data

US 2023/0248720 A1 Aug. 10, 2023

Related U.S. Application Data

(62) Division of application No. 15/332,592, filed on Oct. 24, 2016, now Pat. No. 11,596,628.

(60) Provisional application No. 62/276,658, filed on Jan. 8, 2016.

(51) Int. Cl.

| | |
|---|---|
| ***A61K 31/496*** | (2006.01) |
| ***A61K 9/00*** | (2006.01) |
| ***A61K 9/08*** | (2006.01) |
| ***A61K 9/10*** | (2006.01) |
| ***A61K 31/495*** | (2006.01) |
| ***A61K 31/5415*** | (2006.01) |
| ***A61K 31/675*** | (2006.01) |
| ***A61K 47/10*** | (2017.01) |
| ***A61K 47/14*** | (2017.01) |
| ***A61K 47/20*** | (2006.01) |
| ***A61K 47/22*** | (2006.01) |
| ***A61K 47/26*** | (2006.01) |
| ***A61K 47/34*** | (2017.01) |
| ***A61K 47/44*** | (2017.01) |

(52) U.S. Cl.

CPC .......... *A61K 31/496* (2013.01); *A61K 9/0019* (2013.01); *A61K 9/08* (2013.01); *A61K 9/10* (2013.01); *A61K 31/495* (2013.01); *A61K 31/5415* (2013.01); *A61K 31/675* (2013.01); *A61K 47/10* (2013.01); *A61K 47/14* (2013.01); *A61K 47/20* (2013.01); *A61K 47/22* (2013.01); *A61K 47/26* (2013.01); *A61K 47/34* (2013.01); *A61K 47/44* (2013.01)

(58) Field of Classification Search

CPC ................ A61K 31/495; A61K 31/496; A61K 31/5415; A61K 31/675; A61K 47/10; A61K 47/14; A61K 47/20; A61K 47/22; A61K 47/26; A61K 47/34; A61K 47/44; A61K 9/0019; A61K 9/08; A61K 9/10; A61P 33/10

See application file for complete search history.

(56) References Cited

U.S. PATENT DOCUMENTS

| | | | |
|---|---|---|---|
| 4,772,271 | A | 9/1988 | Meyer et al. |
| 2002/0022667 | A1 | 2/2002 | Pace et al. |
| 2002/0160967 | A1 | 10/2002 | Grosse-Bley et al. |
| 2003/0027858 | A1 | 2/2003 | Lambert et al. |
| 2003/0113372 | A1 | 6/2003 | Hu et al. |
| 2006/0154918 | A1 | 7/2006 | Liversidge et al. |
| 2008/0247957 | A1 | 10/2008 | Wheatley |
| 2009/0286805 | A1 | 11/2009 | Otoda et al. |
| 2010/0125060 | A1 | 5/2010 | Razzak et al. |
| 2011/0319375 | A1 | 12/2011 | Lichter et al. |
| 2012/0238552 | A1 | 9/2012 | Perry et al. |
| 2013/0267504 | A1 | 10/2013 | Perry et al. |
| 2014/0308352 | A1 | 10/2014 | Wright et al. |

FOREIGN PATENT DOCUMENTS

| | | | |
|---|---|---|---|
| EP | 1891956 | A1 | 2/2008 |
| WO | 2002/066006 | A1 | 8/2002 |
| WO | 2009/061607 | A1 | 5/2009 |
| WO | 2010/094623 | A1 | 8/2010 |

OTHER PUBLICATIONS

Chang et al , "Parenteral sustained-release dosage forms of butorplianol for dogs," International Journal of Pharmaceutics 176(2):147-156 (1999).
Keefer et al., "Dosage forms of penicillin for systemic infections," American Journal of Medicine 7(2):216-220 (1949).
International Search Report and Written Opinion of the International Search Authority, mailed Jan. 17, 2017 for PCT/US2016/58437.
Nippe et al., "Evaluation of the in vitro release and pharmacokinetics of parenteral injectable formulations for steroids," European Journal of Pharmaceutics and Biopharmaceutics 83(2):253-265 (2012).
PharmPK Discussion pp. 1-6 (2006).

(Continued)

*Primary Examiner* — Brian-Yong S Kwon
*Assistant Examiner* — Lyndsey M Beckhardt
(74) *Attorney, Agent, or Firm* — MEDLER FERRO WOODHOUSE & MILLS PLLC

(57) ABSTRACT

The invention relates to extended-release formulations comprising: (i) a poorly water-soluble active pharmaceutical ingredient; and (ii) a non-aqueous liquid vehicle comprising (a) a hydrophobic lipid comprising a glyceryl ester of a $C_6$-$C_{24}$ fatty acid, or (b) a hydrophilic organic compound selected from the group consisting of polyethylene glycol, propylene glycol, glycerin, and dimethylsulfoxide, or (c) a combination of (a) and (b), and (iii) an amphiphilic agent wherein the active pharmaceutical ingredient is dispersed as discrete panicles having a $D_{90}$ particle size of about 0.5 μm to about 25 μm in the formulation, and wherein the formulation is non-gelling and thixotropic with a viscosity of less than 10 poise at a shear rate of 10/s at 25° C.

9 Claims, 15 Drawing Sheets

(56) References Cited

OTHER PUBLICATIONS

PubChem Donepezil, accessed Jul. 28, 2021, pp. 1-92 (2021).
PubChem Lurasidone hydrochloride, accessed Jul. 28, 2021, pp. 1-66 (2021).
Wei et al., "Oily nanosuspension for long-acting intramuscular delivery of curcumin didecanoate prodrug: Preparation, characterization and in vivo evaluation," European Journal Pharmaceutical Sciences 49(2):286-293 (2013).

LONG ACTING INJECTABLE FORMULATIONS

FIELD OF THE INVENTION

The field of the invention relates to non-aqueous long acting injectable formulations. Specifically, the invention relates to long acting formulations comprising (i) a poorly water-soluble active pharmaceutical ingredient; and (ii) a non-aqueous liquid vehicle comprising (a) a hydrophobic lipid comprising a glyceryl ester of a $C_6$-$C_{24}$ fatty acid, (b) a hydrophilic organic compound selected from the group consisting of polyethylene glycol, propylene glycol, glycerin, and dimethylsulfoxide, or (c) a combination of (a) and (b), and (iii) an amphiphilic agent, wherein the active pharmaceutical ingredient is dispersed as discrete particles having a $D_{90}$ particle size of about 0.5 μm to about 25 μm in the formulation, and wherein the formulation is non-gelling and thixotropic with a viscosity of less than 10 poise at a shear rate of 10/s at 25° C.

BACKGROUND OF THE INVENTION

More than 150 million (about 2.4%) of world population has been diagnosed with schizophrenia and bipolar syndrome. Approximately 3 million (7.2 out of 1000) individuals in the United States (U.S.) reportedly suffer from schizophrenia, and the United States has a lifetime rate of schizophrenia bipolar disorder at 4.4%. People with schizophrenia and bipolar disorder are at risk for substance abuse and suicide, and treatments include psychiatric care and medication. Bipolar disorders and schizophrenia are chronic conditions. Approximately 10-20% of people with a bipolar disorder commit suicide while many more attempt suicide unsuccessfully. Fortunately, the worst symptoms may be controlled and stabilized with proper medication, and with adherence to the prescribed regimens.

In spite of recent progress in the treatment of schizophrenia and bipolar syndrome, non-adherence to medication regimens, reportedly estimated to be as high as 72%, continues to be a frequent phenomenon. Patient non-compliance to medication regimens is a cause of impairment, hospitalization, higher risk of suicide, longer time to remission, poorer prognosis, unemployment, dangerous behavior, arrest, violence, drug and alcohol consumption, psychiatric emergencies, poor mental performance and may be associated with high costs. For example, the reported national re-hospitalization cost in the U.S., attributable to non-adherence with antipsychotic medications was estimated at approximately $1.5 trillion per year in 2005 (Sun et al, *Curr. Med. Res. Opin.* 2007 October; 23(10):2305-12). Thus the effective management of schizophrenia and bipolar syndrome calls for compliance with medication regimens. Use of a long acting injectable product provides very high assurance of patient compliance in addition to many other advantages when compared with conventional formulations of the same compounds. These advantages include: a predictable drug-release profile during a defined period of time following each injection; improved systemic availability by avoidance of first-pass metabolism; reduced dosing frequency (i.e., fewer injections) without compromising the effectiveness of the treatment; decreased incidence of side effects; and overall cost reduction of medical care.

Lurasidone is an atypical antipsychotic drug belonging to the chemical class of benzisothiazol derivatives. Latuda® Lurasidone Hydrochloride (HCl), immediate-release Tablets, produced by Sunovion Pharmaceuticals Inc., is marketed in the U.S. as an atypical antipsychotic drug for the treatment of schizophrenia and depressive episodes associated with bipolar I disorder (bipolar depression).

Unlike other atypical antipsychotics including, clozapine, olanzapine, and quetiapine that have moderate to high metabolic effects, lurasidone has low metabolic effects including low weight gain, low diabetes risk and low dyslipidemia risk (Citrome L., *Clin Schizophr Relat Psychoses* 2011; 4:251-7; Leucht et al, *Lancet* 2013; 382:951-62). In contrast to aripiprazole, asenapine, iloperidone, olanzapine, paliperidone, quetiapine, risperidone, and ziprasidone which can lead to a prolongation of QT interval (the time between the start of the Q wave and the end of the T wave in the heart's electrical cycle) and cause cardiac arrhythmias; the risk of QT interval prolongation is lower with lurasidone, and lurasidone can be used with patients who have long QT intervals, a history of cardiac arrhythmias, or with medications that prolong the QT interval (www.accessdata.fda.gov/drugsatfda_docs/label/2013/200603_lbls_10s11.pdf).

In addition to the benefits of increased medication compliance attained through the proper formulation of a long acting injection dosage form, an injectable formulation may also increase the bioavailability of lurasidone. The oral bioavailability of the currently marketed Latuda® Lurasidone HCl, immediate-release Tablets is about 9% to 19% due to high first pass effect (www.tga.gov.au/auspar/auspar-lurasidone-hydrochloride). Because the bioavailability of drugs can be improved via the injectable route of administration, an extended-release long acting lurasidone injectable formulation may provide a higher level of bioavailability after intramuscular or subcutaneous administration (≥75%) than the oral route (howmed.net/pharmacology/bioavailability-of-drugs). The increase in bioavailability of an injectable formulation can provide therapeutic plasma concentration levels with a dose that can be administered intramuscularly or subcutaneously once every week, once every month, or once every three months. Owing to the improved bioavailability, the total injected dose can be much lower than the daily dose required over the same time period, thus reducing toxicity and improving patient compliance.

There are several long acting injectable atypical antipsychotic products on the market, specifically, Ability® Aripiprazole extended release injection produced by Otsuka America Pharmaceutical, Inc., Invega Sustenna® and Invega Trinza® Paliperidone Palmitate extended release injections produced by Janssen Pharmaceuticals, Inc. and Risperidal Consta® Risperidone long acting injection produced by Janssen Pharmaceuticals. These dosage forms consist of drug particles as a powder (Abilify®) or aqueous suspension (Invega Sustenna® and Trinza®) or drug embedded in biodegradable polymer matrix (Risperidal Consta®) particles as powder to be dispersed or ready to use as suspensions of particles in aqueous media. Although aqueous media is commonly used in injectable dosage forms, such media has drawbacks including chemical instability through hydrolytic reactions, particle agglomeration and crystal growth, particle sedimentation due to the low viscosity of water, variation of pH and tonicity, and microbial growth in the dosage form.

A non-aqueous formulation, primarily oil-based, may overcome some of the drawbacks of aqueous-based formulations. Examples of oil-based long acting injections include formulations wherein the drug is solubilized in vegetable oil, e.g., Depo-Testosterone® testosterone cypionate (Pfizer), Haldol Deconate® haloperidol deconate (Ortho-McNeil Neurologics), and Fasoldex® fulvestrant (AstraZeneca). Previously, oil-based injectable formulations were not used for drugs insoluble in oils. Since oil-based formulations tend to have higher viscosities, addition of insoluble particles, e.g., suspended particles, may further increase viscosity and render the formulations non-syringeable and non-injectable. To date, the oil-based injectables are applicable only to drugs that are soluble in oil-based vehicles.

SUMMARY OF THE INVENTION

The present invention provides a long acting injectable formulation of a poorly water soluble active pharmaceutical ingredient (API) dispersed in a non-aqueous liquid vehicle. The present invention provides a long acting injectable formulation for intramuscular or subcutaneous administration in patients with psychopathological symptoms that helps overcome the non-adherence problems.

In some embodiments, the invention is directed to a long acting injectable formulation comprising: (i) about 1% to about 50% of a poorly water-soluble active pharmaceutical ingredient; and (ii) about 40% to about 99% of a non-aqueous liquid vehicle comprising (a) a hydrophobic lipid comprising a glyceryl ester of a $C_6$-$C_{24}$ fatty acid, (b) a hydrophilic organic compound selected from the group consisting of polyethylene glycol, propylene glycol, glycerin, and dimethylsulfoxide, or a combination of (a) and (b), and (iii) about 0.5% to 50% of an amphiphilic agent, wherein the active pharmaceutical ingredient is dispersed as discrete particles having a $D_{90}$ particle size of about 0.5 μm to about 25 μm in the formulation, and wherein the formulation is non-gelling and thixotropic with a viscosity of less than 10 poise at a shear rate of 10/s at 25° C.

In some embodiments, the hydrophobic lipid comprises a glyceryl ester of a $C_6$-$C_{24}$ fatty acid. In some embodiments, the hydrophobic lipid is a glyceryl ester of a $C_{12}$-$C_{18}$ fatty acid. In some embodiments, the hydrophobic lipid is selected from the group consisting of castor oil, cottonseed oil, olive oil, peanut oil, safflower oil, sesame oil, soybean oil, coconut oil, palm seed oil, and combinations thereof. In some embodiments, the hydrophobic lipid is sesame oil.

In some embodiments, the hydrophilic organic compound is selected from the group consisting of polyethylene glycol, propylene glycol, glycerin, and dimethylsulfoxide. In some embodiments, the hydrophilic organic compound is polyethylene glycol or propylene glycol. In some embodiments, the hydrophilic organic compound is polyethylene glycol.

In some embodiments, the active pharmaceutical ingredient is an anti-psychotic drug selected from the group consisting of a free base, salt or ester of lurasidone, aripiprazole, asenapine, iloperidone, olanzapine, paliperidone, risperidone, ziprasidone, cariprazine, brexpiprazole, vortioxetine, vilazodone, duloxentine, and mirtazapine. In some embodiments, the active pharmaceutical ingredient is a free base or salt of lurasidone. In some embodiments, the active pharmaceutical ingredient is a free base or salt of cariprazine. In some embodiments, the active pharmaceutical ingredient is a free base, salt or ester of brexpiprazole.

In some embodiments, the active pharmaceutical ingredient in an analgesic. In some embodiments, the analgesic is selected from the group consisting of a free acid, salt or ester of celecoxib, meloxicam, diclofenac, naproxen, ketoprofen, etoricoxib, rofecoxib and tofacitinib. In some embodiments, the analgesic is a free acid, salt or ester of celecoxib. In some embodiments, the analgesic is a free acid, salt or ester of meloxicam.

In some embodiments, the active pharmaceutical ingredient is an antiviral drug. In some embodiments the antiviral drug selected from the group of the poorly soluble salt, or ester of adefovir, entecavir, lamivudine, velpatasvir, rilpivirine and combinations thereof. In some embodiments, the antiviral drug is the poorly soluble salt or ester of adefovir. In some embodiments, the antiviral drug is the poorly soluble salt or ester of entecavir. In some embodiments, the antiviral drug is the poorly soluble salt or ester of lamivudine.

In some embodiments, the active pharmaceutical ingredient in an antibiotic. In some embodiments, the antibiotic is selected from the group consisting of cefditoren and cefpodixime. In some embodiments, the antibiotic is the free acid, salt or ester of cefditoren, for example cefditoren pivoxil. In some embodiments, the antibiotic is the free acid, salt or ester of cefpodixime, for example cefpodoxime proxetil.

In some embodiments, the active pharmaceutical ingredient is provided for the treatment of Alzheimer's disease. In some embodiments, the active pharmaceutical ingredient is selected from the group consisting of free base, poorly soluble salt, or amide of donepezil, galantamine, rivastigmine, and memantine. In some embodiments, the active pharmaceutical ingredient for the treatment of Alzheimer's is the free base or poorly soluble salt of donepezil. In some embodiments, the active pharmaceutical ingredient for the treatment of Alzheimer's is the free base or poorly soluble salt of galantamine. In some embodiments, the active pharmaceutical ingredient for the treatment of Alzheimer's is the free base or poorly soluble salt of rivastigmine. In some embodiments, the active pharmaceutical ingredient for the treatment of Alzheimer's disease is the free base, poorly soluble salt, or amide of memantine.

In some embodiments, the active pharmaceutical ingredient has a $D_{90}$ particle size of about 0.5 μm to about 25 μm. In some embodiments, the active pharmaceutical ingredient has a $D_{90}$ particle size of about 0.5 μm to about 20 μm. In some embodiments, the active pharmaceutical ingredient has a $D_{90}$ particle size of about 0.5 μm to about 15 μm. In some embodiments, the active pharmaceutical ingredient has a $D_{90}$ particle size of about 0.5 μm to about 10 μm.

In some embodiments, the active pharmaceutical ingredient has a $D_{50}$ particle size of about 0.3 μm to about 15 μm. In some embodiments, the active pharmaceutical ingredient has a $D_{50}$ particle size of about 0.3 μm to about 10 μm. In some embodiments, the active pharmaceutical ingredient has a $D_{50}$ particle size of about 0.3 μm to about 5 μm.

In some embodiments, the amphiphilic agent is selected from the group consisting of sorbitan esters, polyethoxylated sorbitan esters, fatty alcohol ethoxylates, fatty acid ethoxylates, castor oil based ethoxylates, polyoxyethylene-polyoxypropylene block copolymers, benzyl alcohol, benzyl benzoate, N-methyl-2-pyrrolidone, dimethylacetamide, ethanol, Vitamin E TPGS, and combinations thereof.

In some embodiments, the vehicle further comprises a preservative selected from the group consisting of butylated hydroxyltoluene (BHT), butylated hydroxyanisole (BHA), propyl gallate, methylparaben, propylparaben, tocopherols and combinations thereof.

In some embodiments, the formulation has a viscosity of about 0.5 poise to about 50 poise at a shear rate of 1/s at 25° C. In some embodiments, the formulation has a viscosity of about 0.5 poise to about 10 poise at a shear rate of 10/s at 25° C. In some embodiments, the formulation has a viscosity of about 0.5 poise to about 4 poise at 100/s shear rate at 25° C.

In some embodiments, the invention is directed to a long acting injectable formulation comprising (i) about 1% to about 50% of lurasidone as free base or salt; (ii) about 40% to about 99% of a hydrophobic lipid vehicle comprising a glyceryl ester of a $C_6$-$C_{24}$ fatty acid, and (iii) about 0.5% to about 50% of an amphiphilic agent, wherein the lurasidone is dispersed as discrete particles having a $D_{90}$ particle size of about 0.5 μm to about 25 μm in the vehicle, and wherein the formulation is non-gelling and thixotropic with a viscosity of less than about 10 poise at a shear rate of 10/s at 25° C. In some embodiments, the amphiphilic agent is/are sorbitan ester(s). In some embodiments, the hydrophobic lipid vehicle is sesame oil.

In some embodiments, the invention is directed to a long acting injectable formulation comprising: (i) about 1% to about 50% of lurasidone as free base or salt; (ii) about 40% to about 99% of a vehicle comprising a hydrophilic organic compound comprising polyethylene glycol or propylene glycol, and (iii) about 0.5% to about 50% of an amphiphilic agent, wherein the lurasidone is dispersed as discrete particles having a $D_{90}$ particle size of about 0.5 μm to about 25 μm in the vehicle, and wherein the formulation is non-gelling and thixotropic with a viscosity of less than about 10 poise at a shear rate of 10/s at 25° C. In some embodiments, the amphiphilic agent is polyethoxylated sorbitan esters. In some embodiments, the hydrophilic organic compound is polyethylene glycol or propylene glycol.

In some embodiments, the invention is directed to a long acting injectable formulation comprising: (i) about 1% to about 50% of lurasidone as free base or salt; (ii) about 40% to about 99% of a non-aqueous liquid vehicle comprising (a) a hydrophobic lipid comprising a glyceryl ester of a $C_6$-$C_{24}$ fatty acid, (b) a hydrophilic organic compound selected from the group consisting of polyethylene glycol, propylene glycol, and/or glycerin, or a combination of (a) and (b); and (iii) about 0.5% to about 50% of an amphiphilic agent, wherein the lurasidone is dispersed as discrete particles having a $D_{90}$ particle size of about 0.5 μm to about 25 μm in the vehicle, and wherein the formulation is non-gelling and thixotropic with a viscosity of less than about 10 poise at a shear rate of 10/s at 25° C. In some embodiments, the amphiphilic agent is polyethoxylated sorbitan esters. In some embodiments, the amphiphilic agent is sorbitan esters. In some embodiments, the hydrophilic organic compound is polyethylene glycol or propylene glycol. In some embodiments, the hydrophobic lipid is sesame oil.

In some embodiments, the invention is directed to a long acting injectable formulation comprising (i) about 1% to about 50% of cariprazine as free base or salt; (ii) about 40% to about 99% of a hydrophobic lipid vehicle comprising a glyceryl ester of a $C_6$-$C_{24}$ fatty acid, and (iii) about 0.5% to about 50% of an amphiphilic agent, wherein the cariprazine is dispersed as discrete particles having a $D_{90}$ particle size of about 0.5 μm to about 25 μm in the vehicle, and wherein the formulation is non-gelling and thixotropic with a viscosity of less than about 10 poise at a shear rate of 10/s at 25° C. In some embodiments, the amphiphilic agent is/are sorbitan ester(s). In some embodiments, the hydrophobic lipid vehicle is sesame oil.

In some embodiments, the invention is directed to a long acting injectable formulation comprising: (i) about 1% to about 50% of cariprazine as free base or salt; (ii) about 40% to about 99% of a vehicle comprising a hydrophilic organic compound comprising polyethylene glycol or propylene glycol, and (iii) about 0.5% to about 50% of an amphiphilic agent, wherein the cariprazine is dispersed as discrete particles having a $D_{90}$ particle size of about 0.5 μm to about 25 μm in the vehicle, and wherein the formulation is non-gelling and thixotropic with a viscosity of less than about 10 poise at a shear rate of 10/s at 25° C. In some embodiments, the amphiphilic agent is polyethoxylated sorbitan esters. In some embodiments, the hydrophilic organic compound is polyethylene glycol or propylene glycol.

In some embodiments, the invention is directed to a long acting injectable formulation comprising: (i) about 1% to about 50% of cariprazine as free base or salt; (ii) about 40% to about 99% of a non-aqueous liquid vehicle comprising (a) a hydrophobic lipid comprising a glyceryl ester of a $C_6$-$C_{24}$ fatty acid, (b) a hydrophilic organic compound selected from the group consisting of polyethylene glycol, propylene glycol, and/or glycerin, or a combination of (a) and (b); and (iii) about 0.5% to about 50% of an amphiphilic agent, wherein the cariprazine is dispersed as discrete particles having a $D_{90}$ particle size of about 0.5 μm to about 25 μm in the vehicle, and wherein the formulation is non-gelling and thixotropic with a viscosity of less than about 10 poise at a shear rate of 10/s at 25° C. In some embodiments, the amphiphilic agent is polyethoxylated sorbitan esters. In some embodiments, the amphiphilic agent is sorbitan esters. In some embodiments, the hydrophilic organic compound is polyethylene glycol or propylene glycol. In some embodiments, the hydrophobic lipid is sesame oil.

In some embodiments, the invention is directed to a long acting injectable formulation comprising (i) about 1% to about 50% of brexpiprazole as free base, salt or ester; (ii) about 40% to about 99% of a hydrophobic lipid vehicle comprising a glyceryl ester of a $C_6$-$C_{24}$ fatty acid, and (iii) about 0.5% to about 50% of an amphiphilic agent, wherein the brexpiprazole is dispersed as discrete particles having a $D_{90}$ particle size of about 0.5 μm to about 25 μm in the vehicle, and wherein the formulation is non-gelling and thixotropic with a viscosity of less than about 10 poise at a shear rate of 10/s at 25° C. In some embodiments, the amphiphilic agent is/are sorbitan ester(s). In some embodiments, the hydrophobic lipid vehicle is sesame oil.

In some embodiments, the invention is directed to a long acting injectable formulation comprising: (i) about 1% to about 50% of brexpiprazole as free base, salt or ester; (ii) about 40% to about 99% of a vehicle comprising a hydrophilic organic compound comprising polyethylene glycol or propylene glycol, and (iii) about 0.5% to about 50% of an amphiphilic agent, wherein the brexpiprazole is dispersed as discrete particles having a $D_{90}$ particle size of about 0.5 μm to about 25 μm in the vehicle, and wherein the formulation is non-gelling and thixotropic with a viscosity of less than about 10 poise at a shear rate of 10/s at 25° C. In some embodiments, the amphiphilic agent is polyethoxylated sorbitan esters. In some embodiments, the hydrophilic organic compound is polyethylene glycol or propylene glycol.

In some embodiments, the invention is directed to a long acting injectable formulation comprising: (i) about 1% to about 50% of brexpiprazole as free base, salt or ester; (ii) about 40% to about 99% of a non-aqueous liquid vehicle comprising (a) a hydrophobic lipid comprising a glyceryl ester of a $C_6$-$C_{24}$ fatty acid, (b) a hydrophilic organic compound selected from the group consisting of polyethylene glycol, propylene glycol, and/or glycerin, or a combination of (a) and (b); and (iii) about 0.5% to about 50% of an amphiphilic agent, wherein the brexpiprazole is dispersed as discrete particles having a $D_{90}$ particle size of about 0.5 μm to about 25 μm in the vehicle, and wherein the formulation is non-gelling and thixotropic with a viscosity of less than about 10 poise at a shear rate of 10/s at 25° C. In some embodiments, the amphiphilic agent is polyethoxylated sorbitan esters. In some embodiments, the amphiphilic agent is sorbitan esters. In some embodiments, the hydrophilic organic compound is polyethylene glycol or propylene glycol. In some embodiments, the hydrophobic lipid is sesame oil.

In some embodiments, the invention is directed to a process for preparing a long acting injectable formulation, comprising: (i) mixing an amphiphilic agent with a non-aqueous liquid vehicle comprising (a) a hydrophobic lipid comprising a glyceryl ester of a $C_6$-$C_{24}$ fatty acid, (b) a hydrophilic organic compound selected from the group consisting of polyethylene glycol, propylene glycol, glycerin, and dimethylsulfoxide, or a combination of (a) and (b); (ii) dispersing a poorly water-soluble active pharmaceutical ingredient in the mixture of (i) and mixing to form a dispersion; (iii) milling the dispersion of (ii) to achieve an active pharmaceutical ingredient having a $D_{90}$ particle size of about 0.5 μm to about 25 μm to obtain the long acting injectable formulation.

In some embodiments, the present invention is directed to a process for preparing a long acting injectable formulation, comprising: (i) mixing an amphiphilic agent with a non-aqueous liquid vehicle comprising (a) a hydrophobic lipid comprising a glyceryl ester of a $C_6$-$C_{24}$ fatty acid, (b) a hydrophilic organic compound selected from the group consisting of polyethylene glycol, propylene glycol, glycerin, and dimethylsulfoxide, or a combination of (a) and (b); (ii) dispersing a poorly water-soluble active pharmaceutical ingredient having a $D_{90}$ particle size of about 0.5 μm to about 25 μm in the mixture of (i) and mixing to form a uniform dispersion to obtain the long acting injectable formulation In some embodiments, the method of the invention further comprises adding excipients to form a final dosage form.

In some embodiments, the method of the invention is directed to a process for preparing a long acting injectable formulation, wherein the active pharmaceutical ingredient is an anti-psychotic drug selected from the group consisting of free base, salt or ester of lurasidone, aripiprazole, asenapine, iloperidone, olanzapine, paliperidone, risperidone, ziprasidone, cariprazine, brexpiprazole, vortioxetine, vilazodone, duloxentine, and mirtazapine.

In some embodiments, the invention is directed to an injectable pharmaceutical dosage form, comprising (i) a long acting injectable formulation as described herein, and (ii) a pre-filled syringe or vial.

In some embodiments, the invention is directed to a method of administering a poorly soluble active pharmaceutical ingredient to a subject, the method comprising administering intramuscularly or subcutaneously a long acting injectable formulation as described herein.

In some embodiments, the invention is directed to a method of treating a psychotic disorder, the method comprising administering intramuscularly or subcutaneously a long acting injectable formulation as described herein.

In some embodiments, the invention is directed to a method as described herein comprising administering a long acting injectable formulation as described herein once a week. In some embodiments, the invention is directed to a method as described herein comprising administering a long acting injectable formulation as described herein once a month. In some embodiments, the invention is directed to a method as described herein comprising administering a long acting injectable formulation as described herein once every three months.

In some embodiments, the invention is directed to a method as described herein comprising administering a long acting injectable formulation comprising an anti-psychotic drug selected from the group consisting of free base, salt or ester of lurasidone, aripiprazole, asenapine, iloperidone, olanzapine, paliperidone, risperidone, ziprasidone, cariprazine, brexpiprazole, vortioxetine, vilazodone, duloxentine, and mirtazapine.

In some embodiments, the invention is directed to a method as described herein comprising an active pharmaceutical ingredient that is a free base or salt of lurasidone.

In some embodiments, the invention is directed to a method as described herein comprising an active pharmaceutical ingredient that is a free base or salt of cariprazine.

In some embodiments, the invention is directed to a method as described herein comprising an active pharmaceutical ingredient that is a free base, salt or ester of brexpiprazole.

DETAILED DESCRIPTION OF THE INVENTION

Figure 1:
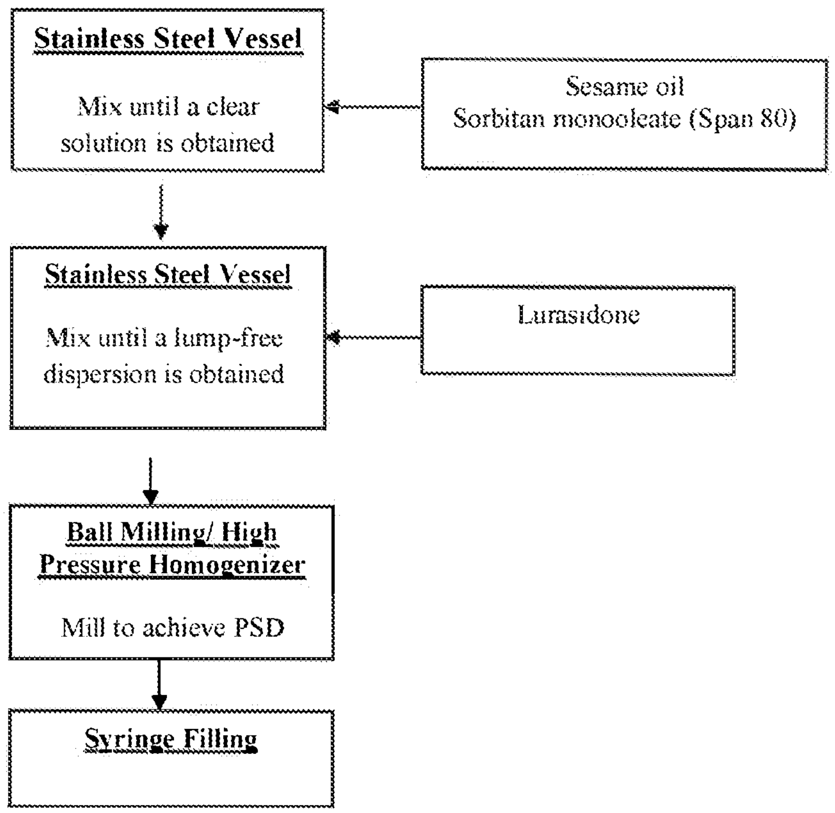
FIG. 1 depicts a representative flow chart for making a long acting injectable formulation of lurasidone in a non-aqueous hydrophobic lipid vehicle, using a wet milling process of ball/media or high pressure homogenizer milling.

The invention presented herein relates to a long acting injectable formulation of a poorly water soluble active pharmaceutical ingredient dispersed in a non-aqueous liquid vehicle. In addition, the invention presented herein relates to processes for preparing the long acting injectable formulation as described herein, and uses thereof.

In some embodiments, the invention is directed to a long acting injectable formulation comprising: (i) a poorly water-soluble active pharmaceutical ingredient; and (ii) a non-aqueous liquid vehicle comprising (a) a hydrophobic lipid comprising a glyceryl ester of a $C_6$-$C_{24}$ fatty acid or (b) a hydrophilic organic compound, or a combination of (a) and (b) and (iii) an amphiphilic agent, wherein the active pharmaceutical ingredient is dispersed as discrete particles having a $D_{90}$ particle size of about 0.5 μm to about 25 μm in the formulation, and wherein the formulation is non-gelling and thixotropic with a viscosity of less than 10 poise at a shear rate of 10/s at 25° C.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the method/device being employed to determine the value, or the variation that exists among the study subjects. Typically the term is meant to encompass approximately or less than 1%, 5%, 10%, 15% or 20% variability depending on the situation.

The use of the term "or" in the claims is used to mean "and/or" unless explicitly indicated to refer only to alternatives or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited, elements or method steps. It is contemplated that any embodiment discussed in this specification can be implemented with respect to any method and/or formulation of the invention.

The use of the term "for example" and its corresponding abbreviation "e.g." (whether italicized or not) means that the specific terms recited are representative examples and embodiments of the invention that are not intended to be limited to the specific examples referenced or cited unless explicitly stated otherwise.

The term "long acting" as used herein refers to a dosage formulation that provides for the release of a drug over an extended period of time. In some embodiments, the release of a drug will occur over a period greater than about 1 day. In some embodiments, the release of a drug will occur over a period greater than about 2 days. In some embodiments, the release of a drug will occur over a period greater than about 3 days. In some embodiments, the release of a drug will occur over a period greater than about 4 days. In some embodiments, the release of a drug will occur over a period greater than about 5 days. In some embodiments, the release of a drug will occur over a period greater than about 6 days. In some embodiments, the release of a drug will occur over a period greater than about 1 week. In some embodiments, the release of a drug will occur over a period greater than about 2 weeks. In some embodiments, the release of a drug will occur over a period greater than about 3 weeks. In some embodiments, the release of a drug will occur over a period greater than about 4 weeks. In some embodiments, the release of a drug will occur over a period greater than about 5 weeks. In some embodiments, the release of a drug will occur over a period greater than about 6 weeks. In some embodiments, the release of a drug will occur over a period greater than about 8 weeks. In some embodiments, the release of a drug will occur over a period greater than about 10 weeks. In some embodiments, the release of a drug will occur over a period greater than about 12 weeks. In some embodiments, the release of a drug will occur over a period greater than about 18 weeks. In some embodiments, the release of a drug will occur over a period greater than about 24 weeks. In some embodiments, the release of a drug will occur over a period greater than about 30 weeks. In some embodiments, the release of a drug will occur over a period greater than about 1 month. In some embodiments, the release of a drug will occur over a period greater than about 2 months. In some embodiments, the release of a drug will occur over a period greater than about 3 months. In some embodiments, the release of a drug will occur over a period greater than about 4 months. In some embodiments, the release of a drug will occur over a period of about 1 day to about 4 months. In some embodiments, the release of a drug will occur over a period of about 1 day to about 3 months. In some embodiments, the release of a drug will occur over a period of about 1 week to about 4 months. In some embodiments, the release of a drug will occur over a period of about 1 week to about 3 months. In some embodiments, the release of a drug will occur over a period of about 1 week to about 2 months. In some embodiments, the release of a drug will occur over a period of about 1 week to about 1 month. In some embodiments, the release of a drug will occur over a period of about 2 weeks to about 3 months. In some embodiments, the release of a drug will occur over a period of about 2 weeks to about 2 months. In some embodiments, the release of a drug will occur over a period of about 2 weeks to about 1 month. In some embodiments, the release of a drug will occur over a period of about 3 weeks to about 3 month. In some embodiments, the release of a drug will occur over a period of about 1 month to about 2 months.

In some embodiments, the term "long acting" refers to a release profile wherein the plasma concentration of the Active Pharmaceutical Ingredient (API) is maintained at steady state for an extended period of time. In some embodiments, the plasma concentration of the API is maintained at steady state over a period greater than about 1 day. In some embodiments, the plasma concentration of the API is maintained at steady state over a period greater than about 2 days. In some embodiments, the plasma concentration of the API is maintained at steady state over a period greater than about 3 days. In some embodiments, the plasma concentration of the API is maintained at steady state over a period greater than about 4 days. In some embodiments, the plasma concentration of the API is maintained at steady state over a period greater than about 5 days. In some embodiments, the plasma concentration of the API is maintained at steady state over a period greater than about 6 days. In some embodiments, the plasma concentration of the API is maintained at steady state over a period greater than about 1 week. In some embodiments, the plasma concentration of the API is maintained at steady state over a period greater than about 2 weeks. In some embodiments, the plasma concentration of the API is maintained at steady state over a period greater than about 3 weeks. In some embodiments, the plasma concentration of the API is maintained at steady state over a period greater than about 4 weeks. In some embodiments, the plasma concentration of the API is maintained at steady state over a period greater than about 5 weeks. In some embodiments, the plasma concentration of the API is maintained at steady state over a period greater than about 6 weeks. In some embodiments, the plasma concentration of the API is maintained at steady state over a period greater than about 8 weeks. In some embodiments, the plasma concentration of the API is maintained at steady state over a period greater than about 10 weeks. In some embodiments, the plasma concentration of the API is maintained at steady state over a period greater than about 12 weeks. In some embodiments, the plasma concentration of the API is maintained at steady state over a period greater than about 18 weeks. In some embodiments, the plasma concentration of the API is maintained at steady state over a period greater than about 24 weeks. In some embodiments, the plasma concentration of the API is maintained at steady state over a period greater than about 30 weeks. In some embodiments, the plasma concentration of the API is maintained at steady state over a period greater than about 1 month. In some embodiments, the plasma concentration of the API is maintained at steady state over a period greater than about 2 months. In some embodiments, the plasma concentration of the API is maintained at steady state over a period greater than about 3 months. In some embodiments, the plasma concentration of the API is maintained at steady state over a period greater than about 4 months. In some embodiments, the plasma concentration of the API is maintained at steady state over a period of about 1 day to about 4 months. In some embodiments, the plasma concentration of the API is maintained at steady state over a period of about 1 day to about 3 months. In some embodiments, the plasma concentration of the API is maintained at steady state over a period of about 1 week to about 4 months. In some embodiments, the plasma concentration of the API is maintained at steady state over a period of about 1 week to about 3 months. In some embodiments, the plasma concentration of the API is maintained at steady state over a period of about 1 week to about 2 months. In some embodiments, the plasma concentration of the API is maintained at steady state over a period of about 1 week to about 1 month. In some embodiments, the plasma concentration of the API is maintained at steady state over a period of about 2 weeks to about 3 months. In some embodiments, the plasma concentration of the API is maintained at steady state over a period of about 2 weeks to about 2 months. In some embodiments, the plasma concentration of the API is maintained at steady state over a period of about 2 weeks to about 1 month. In some embodiments, the plasma concentration of the API is maintained at steady state over a period of about 3 weeks to about 3 month. In some embodiments, the plasma concentration of the API is maintained at steady state over a period of about 1 month to about 2 months.

In some embodiments, the term "long acting" refers to a release profile wherein the therapeutic effect of the API is maintained for an extended period of time. In some embodiments, the therapeutic effect is maintained for a period greater than about 1 day. In some embodiments, the therapeutic effect is maintained for a period greater than about 2 days. In some embodiments, the therapeutic effect is maintained for a period greater than about 3 days. In some embodiments, the therapeutic effect is maintained for a period greater than about 4 days. In some embodiments, the therapeutic effect is maintained for a period greater than about 5 days. In some embodiments, the therapeutic effect is maintained for a period greater than about 6 days. In some embodiments, the therapeutic effect is maintained for a period greater than about 1 week. In some embodiments, the therapeutic effect is maintained for a period greater than about 2 weeks. In some embodiments, the therapeutic effect is maintained for a period greater than about 3 weeks. In some embodiments, the therapeutic effect is maintained for a period greater than about 4 weeks. In some embodiments, the therapeutic effect is maintained for a period greater than about 5 weeks. In some embodiments, the therapeutic effect is maintained for a period greater than about 6 weeks. In some embodiments, the therapeutic effect is maintained for a period greater than about 8 weeks. In some embodiments, the therapeutic effect is maintained for a period greater than about 10 weeks. In some embodiments, the therapeutic effect is maintained for a period greater than about 12 weeks. In some embodiments, the therapeutic effect is maintained for a period greater than about 18 weeks. In some embodiments, the therapeutic effect is maintained for a period greater than about 24 weeks. In some embodiments, the therapeutic effect is maintained for a period greater than about 30 weeks. In some embodiments, the therapeutic effect is maintained for a period greater than about 1 month. In some embodiments, the therapeutic effect is maintained for a period greater than about 2 months. In some embodiments, the therapeutic effect is maintained for a period greater than about 3 months. In some embodiments, the therapeutic effect is maintained for a period greater than about 4 months. In some embodiments, the therapeutic effect is maintained for a period of about 1 day to about 4 months. In some embodiments, the therapeutic effect is maintained for a period of about 1 day to about 3 months. In some embodiments, the therapeutic effect is maintained for a period of about 1 week to about 4 months. In some embodiments, the therapeutic effect is maintained for a period of about 1 week to about 3 months. In some embodiments, the therapeutic effect is maintained for a period of about 1 week to about 2 months. In some embodiments, the therapeutic effect is maintained for a period of about 1 week to about 1 month. In some embodiments, the therapeutic effect is maintained for a period of about 2 weeks to about 3 months. In some embodiments, the therapeutic effect is maintained for a period of about 2 weeks to about 2 months. In some embodiments, the therapeutic effect is maintained for a period of about 2 weeks to about 1 month. In some embodiments, the therapeutic effect is maintained for a period of about 3 weeks to about 3 month. In some embodiments, the therapeutic effect is maintained for a period of about 1 month to about 2 months.

In some embodiments, the disclosure provides a long acting injectable formulation as described herein, wherein the half-life (t½) of the formulation is increased significantly relative to a regular-release (i.e., non-long acting) dosage form when placed in a subject. For example, the half-life of the long acting injectable formulation as described here is increased significantly in the body relative to an immediate release oral dosage form, or an immediate release injectable formulation. In some embodiments, the term "regular-release" dosage form refers to a dosage form in which the half-life is 1 to 48 hours, or 1 to 24 hours. In some embodiments, the "regular-release" dosage form is a currently marketed immediate-release oral or injectable dosage form. By way of example, the t½ of the formulation of the present disclosure using lurasidone as an active pharmaceutical ingredient would be increased significantly relative to the commercially available lurasidone oral table, e.g., Latuda® (Sunovian Pharmaceuticals, Marlborough, MA).

The term "increased significantly," when referring to half-life, means the half-life is greater than 2 times longer relative to a regular-release dosage form. In some embodiments, the term "increased significantly," when referring to half-life, means the half-life is greater than 3 times, greater than 4 times, greater than 5 times, greater than 6 times, greater than 7 times, greater than 8 times, greater than 9 times, greater than 10 times, greater than 15 times, greater than 20 times or greater than 30 times longer relative to a regular-release dosage form.

In some embodiments, the mean residence time (MRT) of the active pharmaceutical ingredient is increased significantly relative to a regular-release dosage form. Determination of MRT can be calculated by the skilled artisan, and represents the average time a molecule stays in the body. In some embodiments, the term "regular-release" dosage form refers to a dosage form in which the MRT is 1 to 72 hours, 1 to 48 hours, or 1 to 24 hours. In some embodiments, the "regular-release" dosage form is a currently marketed immediate-release oral or injectable dosage form. By way of example, the MRT of the formulation of the present disclosure using lurasidone as an active pharmaceutical ingredient would be increased significantly relative to the commercially available lurasidone oral table, e.g., Latuda® (Sunovian Pharmaceuticals, Marlborough, MA).

The term "increased significantly," when referring to MRT means the MRT is greater than 2 times longer relative to a regular-release dosage form. In some embodiments, the term "increased significantly," when referring to MRT, means the MRT is greater than 3 times, greater than 4 times, greater than 5 times, greater than 6 times, greater than 7 times, greater than 8 times, greater than 9 times, greater than 10 times, greater than 15 times, greater than 20 times or greater than 30 times longer relative to a regular-release dosage form.

In some embodiments, the disclosure provides a long acting injectable formulation as described herein, wherein the ratio of area under the curve (AUC) to the maximum serum concentration of the active pharmaceutical ingredient in the subject ($C_{max}$), is increased significantly relative to a regular-release (i.e., non-long acting) dosage form. For example, the ratio ($AUC/C_{max}$) of the long acting injectable formulation as described here is increased significantly relative to an immediate release oral dosage form, or an immediate release injectable formulation. In some embodiments, the "regular-release" dosage form is a currently marketed immediate-release oral or injectable dosage form. By way of example, the $AUC/C_{max}$ of the formulation of the present disclosure using lurasidone as an active pharmaceutical ingredient would be increased significantly relative to the commercially available lurasidone oral table, e.g., Latuda® (Sunovian Pharmaceuticals, Marlborough, MA).

The term "increased significantly," when referring to $AUC/C_{max}$ means the $AUC/C_{max}$ is greater than 2 times longer relative to a regular-release dosage form. In some embodiments, the term "increased significantly," when referring to $AUC/C_{max}$, means the $AUC/C_{max}$ is greater than 3 times, greater than 4 times, greater than 5 times, greater than 6 times, greater than 7 times, greater than 8 times, greater than 9 times, greater than 10 times, greater than 15 times, greater than 20 times or greater than 30 times longer relative to a regular-release dosage form.

In some embodiments, the pharmacokinetic parameters of the extended-release formulation (the half-life ($t_{1/2}$), the ratio of AUC to $C_{max}$ and the MRT) increase significantly relative to a regular release formulation to minimize dosing frequency in a subject for treatment of disease.

In some embodiments with long acting dosage formulations, the rate of release of the drug from the dosage form may be reduced to maintain therapeutic activity of the drug for a longer period of time or to reduce any toxic effects associated with a particular dosing of the drug. Long acting dosage formulations may have the advantage of providing patients with a dosing regimen that allows for less frequent dosing, thus enhancing compliance. Long acting dosage formulations may also reduce peak-related side effects associated with some drugs and can maintain therapeutic concentrations throughout the dosing period thus avoiding periods of insufficient therapeutic plasma concentrations between doses. In some embodiments, the term "long acting," as used herein, is taken to encompass long acting, extended release, sustained release, controlled release, modified release, prolonged release, delayed release and the like.

The term "injectable" as used herein refers to an aseptic preparation acting in such a way that a commonly injected liquid-phase drug is directly introduced into the body via the skin, muscle, vein, etc. In some embodiments, the term "injectable" refers to subcutaneous and/or intramuscular preparations.

The term "formulation" or "composition" or "dosage form" as used herein refers to physically discrete units, wherein each unit containing a predetermined quantity of active ingredient in association with a pharmaceutically acceptable excipients.

The term "poorly water soluble" as used herein refers to active ingredients which have a solubility of, at room temperature and 1 atmospheric pressure, less than or about 1 mg/ml in water. In some embodiments, the solubility is less than or about 0.5 mg/ml. In some embodiments, the solubility is less than or about 0.1 mg/ml. In some embodiments, the solubility is less than or about 0.05 mg/ml. In some embodiments, the solubility is less than or about 0.01 mg/ml. In some embodiments, the solubility is less than or about 0.001 mg/ml. In some embodiments, the solubility is between about 0.001 mg/ml to about 1 mg/ml. In some embodiments, the solubility is between about 0.008 mg/ml to about 0.5 mg/ml. In some embodiments, the solubility is between about 0.001 mg/ml to about 0.01 mg/ml. In some embodiments, the solubility is between about 0.005 mg/ml to about 0.2 mg/ml. In some embodiments, the solubility is between about 0.005 mg/ml to about 0.1 mg/ml. In some embodiments, the solubility is less than or about 1 mg/ml at a pH of about 5.0, about 6.0 or about 7.0. In some embodiments, the solubility is less than or about 0.5 mg/ml at a pH of about 5.0, about 6.0 or about 7.0. In some embodiments, the solubility is less than or about 0.1 mg/ml at a pH of about 5.0, about 6.0 or about 7.0. In some embodiments, the solubility is less than or about 0.05 mg/ml at a pH of about 5.0, about 6.0 or about 7.0. In some embodiments, the solubility is less than or about 0.01 mg/ml at a pH of about 5.0, about 6.0 or about 7.0. In some embodiments, the solubility is less than or about 0.001 mg/ml at a pH of about 5.0, about 6.0 or about 7.0. In some embodiments, the solubility is between about 0.001 mg/ml to about 1 mg/ml at a pH of about 5.0, about 6.0 or about 7.0. In some embodiments, the solubility is between about 0.008 mg/ml to about 0.5 mg/ml at a pH of about 5.0, about 6.0 or about 7.0. In some embodiments, the solubility is between about 0.001 mg/ml to about 0.01 mg/ml at a pH of about 5.0, about 6.0 or about 7.0. In some embodiments, the solubility is between about 0.005 mg/ml to about 0.2 mg/ml at a pH of about 5.0, about 6.0 or about 7.0. In some embodiments, the solubility is between about 0.005 mg/ml to about 0.1 mg/ml at a pH of about 5.0, about 6.0 or about 7.0. In some embodiments, solubility is determined at a pH of about 7.0. The determination of water solubility is described by the United States Pharmacopeia.

The term "active pharmaceutical ingredient" or "active ingredient" as used herein refers to any component that is intended to furnish pharmacological activity or other direct effect in the diagnosis, cure, mitigation, treatment, or prevention of disease in man or other animals. A suitable example includes, but is not limited to, anti-psychotic drugs.

The term "anti-psychotic drug" as used herein refers to any substance that lessens the symptoms of a psychotic disorder. Suitable examples include, but are not limited to, free base, salt or ester of lurasidone, aripiprazole, asenapine, iloperidone, olanzapine, paliperidone, risperidone, ziprasidone, cariprazine, brexpiprazole, vortioxetine, vilazodone, duloxentine, and mirtazapine. In some embodiments, the term "anti-psychotic drug" refers to a free base or salt of lurasidone. In some embodiments, the term "anti-psychotic drug" refers to a free base or salt of cariprazine. In some embodiments, the term "anti-psychotic drug" refers to a free base, salt or ester of brexpiprazole.

The term "analgesic" as used herein refers to any substance that provides relief from pain or discomfort. In some embodiments, the term analgesic refers to a non-steroidal anti-inflammatory drug (NSAID). In some embodiments, the term analgesic refers to a Cox-2 inhibitor. In some embodiments, the analgesic is selected from the group consisting of the free acid, salt or ester of celecoxib, meloxicam, diclofenac, naproxen, ketoprofen, etoricoxib, rofecoxib and tofacitinib. In some embodiments, the analgesic is the free acid, salt or ester of celecoxib. In some embodiments, the analgesic is the free acid, salt or ester of meloxicam.

The term "antiviral" as used herein refers to any substance that destroys a virus or that suppresses its ability to replicate and, hence, inhibits its capability to multiply and reproduce. In some embodiments, the term antiviral refers to substances that are effective against Hepatitis B virus selected from the group of the poorly soluble salt or ester of adefovir, entecavir, lamivudine, velpatasvir, rilpivirine and combinations thereof. In some embodiments, the antiviral drug is the poorly soluble salt or ester of adefovir. In some embodiments, the antiviral drug is the poorly soluble salt or ester of entecavir. In some embodiments, the antiviral drug is the poorly soluble salt or ester of lamivudine.

The term "antibiotic" as used herein refers to any substance that destroys bacteria or that suppresses its ability to replicate and, hence, inhibits its capability to multiply and reproduce. In some embodiments, the antibiotic is selected from the group consisting of cefditoren and cefpodixime. In some embodiments, the antibiotic is the free acid, salt or ester of cefditoren, for example cefditoren pivoxil. In some embodiments, the antibiotic is the free acid, salt or ester of cefpodixime, for example cefpodoxime proxetil.

The term "treatment of Alzheimer's disease" as used herein refers to any substance that relieves the symptoms of Alzheimer's disease or improves the conditions of subjects with the disease. In some embodiments, the drug for Alzheimer's disease is selected from the group consisting of free base, poorly soluble salt, or amide of donepezil, galantamine, rivastigmine, and memantine. In some embodiments, the active pharmaceutical ingredient for the treatment of Alzheimer's is the free base or poorly soluble salt of donepezil. In some embodiments, the active pharmaceutical ingredient for the treatment of Alzheimer's is the free base or poorly soluble salt of galantamine. In some embodiments, the active pharmaceutical ingredient for the treatment of Alzheimer's is the free base or poorly soluble salt of rivastigmine. In some embodiments, the active pharmaceutical ingredient for the treatment of Alzheimer's disease is the free base, poorly soluble salt, or amide of memantine. The term "antibiotic" as used herein refers to any substance that destroys bacteria or that suppresses its ability to replicate and, hence, inhibits its capability to multiply and reproduce. In some embodiments, the antibiotic is selected from the group consisting of cefditoren and cefpodixime. In some embodiments, the antibiotic is the free acid, salt or ester of cefditoren, for example cefditoren pivoxil. In some embodiments, the antibiotic is the free acid, salt or ester of cefpodixime, for example cefpodoxime proxetil. The term "psychotic disorder" as used herein refers to a disorder in which psychosis is a recognized symptom, this includes neuropsychiatric (psychotic depression and other psychotic episodes) and neurodevelopmental disorders (especially autistic spectrum disorders), neurodegenerative disorders, depression, mania, and in particular, schizophrenic disorders (paranoid, catatonic, disorganized, undifferentiated and residual schizophrenia) and bipolar disorders. Preferably, the invention relates to schizophrenic and bipolar disorders.

The term "non-aqueous liquid" as used herein refers to any liquid comprising less than about 10% by weight of water. In some embodiments, the non-aqueous is any liquid comprising less than about 5% by weight of water. In some embodiments, the non-aqueous is any liquid comprising less than about 3% by weight of water. In some embodiments, the non-aqueous is any liquid comprising less than about 1% by weight of water. In some embodiments, the non-aqueous is any liquid comprising less than about 0.5% by weight of water. In some embodiments, the non-aqueous is any liquid comprising about 10% to about 0.001% by weight of water. In some embodiments, the non-aqueous is any liquid comprising about 5% to about 0.01% by weight of water. In some embodiments, the non-aqueous is any liquid comprising about 1% to about 0.01% by weight of water. In some embodiments, the term "non-aqueous" refers generally to the condition of having little or no water.

The term "vehicle" as used herein refers to any solvent or carrier fluid in a pharmaceutical product that has no pharmacological role. Liquid vehicles may be used in preparing solutions, suspensions, emulsions, syrups, elixirs and pressurized compositions. The agent of the invention can be dispersed or suspended in a pharmaceutically acceptable liquid vehicle such an organic solvent, pharmaceutically acceptable oils or fats, for example. In some embodiments, the liquid pharmaceutical compositions in accordance with the invention are provided as substantially non-aqueous dispersions.

Use of such non-aqueous vehicles provides several advantages over aqueous-based vehicles. APIs can be prone to hydrolysis in aqueous systems (LePree et al., Hydrolysis of Drugs. In Encyclopedia of Pharmaceutical Science and Technology, Fourth Edition. Taylor and Francis: New York, Published online: 23 Aug. 2013; 1895-1900), and formulation in a non-aqueous vehicle may prevent this route of degradation. Aqueous-based systems can be more prone to microbial contamination, and in some embodiments, formulations of such systems frequently must contain anti-microbial agents. Furthermore, owing to the low viscosity of water, in some embodiments, viscosity enhancers must be used in the formulation to prevent particle agglomeration and sedimentation contributing to instability of suspensions.

In some embodiments, the vehicle comprises a non-aqueous hydrophobic lipid. In some embodiments, the non-aqueous liquid vehicle comprises a hydrophilic organic compound. Both non-aqueous hydrophobic lipid vehicle and non-aqueous hydrophilic organic compounds may provide several advantages over aqueous-based vehicles including, but not limited to, enhanced stability through lack of available reactant for hydrolytic decomposition, low likelihood of microbial growth and contamination, and required viscosity needed to prevent settling of suspensions without the need to add substantial quantities of thickening agents.

The term "hydrophobic" as used herein refers to a compound tending to be electrically neutral and non-polar, and thus preferring other neutral and nonpolar solvents or molecular environments. The term "lipid", as used herein, refers to a group of organic compounds that include, but are not limited to, esters of fatty acids and are characterized by being insoluble in water, but soluble in many organic solvents. The term "hydrophobic lipid", as used herein, refers to compounds having apolar groups that include, but are not limited to, long-chain saturated and unsaturated aliphatic hydrocarbon groups and such groups optionally substituted by one or more aromatic, cycloaliphatic, or heterocyclic group(s).

The term "hydrophilic", as used herein, means that something 'likes water', i.e. a hydrophilic molecule is one that typically is capable of forming hydrogen bonds with water molecules, enabling it to dissolve more readily in water. The term "organic compound" refers to chemical compounds comprising carbon, such as a substituted and/or unsubstituted hydrocarbon. Organic compounds may comprise additional elements, such as oxygen, nitrogen, chlorine, etc. Suitable examples of "hydrophilic organic compound" for the invention described herein include, but are not limited to, polyethylene glycol, propylene glycol, glycerin, and dimethylsulfoxide.

In certain embodiments, the non-aqueous hydrophobic lipid vehicle comprises a non-aqueous and non-gel forming hydrophobic lipid. In some embodiments, the hydrophobic lipid comprises glyceryl esters of fatty acids containing predominantly lauric acid ($C_{12}$), myristic acid ($C_{14}$), palmitic acid ($C_{16}$), oleic acid ($C_{18}$), ricinoleic acid ($C_{18}$), and linoleic acid ($C_{18}$) or mixtures thereof along with esters of $C_6$-$C_{24}$ fatty acids. In some embodiments, the hydrophobic lipid is selected from the group consisting of castor oil, cottonseed oil, olive oil, peanut oil, safflower oil, sesame oil, soybean oil, coconut oil, palm seed oil, and combinations thereof. In certain embodiments, the non-aqueous hydrophobic lipid vehicle comprises sesame oil.

In certain embodiments, the non-aqueous and non-gel forming hydrophobic lipid comprises glyceryl esters of a $C_6$-$C_{24}$ fatty acids.

The term "glyceryl ester" as used herein refers to esters of fatty acids and glycerol, or polyglycerol and their derivatives. Glyceryl esters of fatty acids include glyceryl fatty acid ester, glyceryl acetic acid fatty acid ester, glyceryl lactic acid fatty acid ester, glyceryl citric acid fatty acid ester, glyceryl succinic acid fatty acid ester, glyceryl diacetyl tartaric acid fatty acid ester, glyceryl acetic acid ester, polyglyceryl fatty acid ester, and polyglyceryl condensed ricinoleic acid ester. In some embodiments, the term "glyceryl ester" as used herein refers to esters of $C_6$-$C_{24}$ fatty acids. In some embodiments, the term "glyceryl ester" as used herein refers to esters of $C_{12}$-$C_{18}$ fatty acids.

The term "$C_6$-$C_{24}$ fatty acid" as used herein refers to saturated and/or unsaturated carboxylic acids comprising from 6 to 24 carbon atoms. In certain embodiments, the term "$C_6$-$C_{24}$ fatty acid" refers to saturated and/or unsaturated carboxylic acids comprising from 6 carbon atoms, 8 carbon atoms, 10 carbon atoms, 12 carbon atoms, 14 carbon atoms, 16 carbon atoms, 18 carbon atoms, 20 carbon atoms, 22 carbon atoms, and 24 carbon atoms, or mixtures thereof.

In some embodiments, the $C_6$-$C_{24}$ fatty acid can be from a natural source, e.g., from a plant. In some embodiments, the $C_6$-$C_{24}$ fatty acid can be from a synthetic source. In some embodiments, the term "$C_6$-$C_{24}$ fatty acid" refers to saturated and/or unsaturated carboxylic acids comprising greater than about 90% of mixtures of 6 carbon atoms, 8 carbon atoms, 10 carbon atoms, 12 carbon atoms, 14 carbon atoms, 16 carbon atoms, 18 carbon atoms, 20 carbon atoms, 22 carbon atoms, and 24 carbon atoms. In some embodiments, the fatty acid combinations may comprise less than about 1% to less than about 10% of 6 carbon atoms, less than about 10% to less than about 80% of 8 carbon atoms, less than about 10% to less than about 45% of 10 carbon atoms, less than about 5% to less than about 50% of 12 carbon atoms, less than about 1% to less than about 20% of 14 carbon atoms, less than about 0.1% to less than about 50% of 16 carbon atoms, less than about 1% to less than about 90% of 18 carbon atoms, less than about 0.5% to less than about 10% of 20 carbon atoms, less than about 0.5% to less than about 1% of 22 carbon atoms, and less than about 0.1% to less than about 1% of 24 carbon atoms.

In some embodiments, the term "$C_6$-$C_{24}$ fatty acid" refers to saturated and/or unsaturated carboxylic acids comprising $C_8$-$C_{24}$ fatty acids. In some embodiments, the term "$C_6$-$C_{24}$ fatty acid" refers to saturated and/or unsaturated carboxylic acids comprising $C_{10}$-$C_{22}$ fatty acids. In some embodiments, the term "$C_6$-$C_{24}$ fatty acid" refers to saturated and/or unsaturated carboxylic acids comprising $C_8$-$C_{20}$ fatty acids. In some embodiments, the term "$C_6$-$C_{24}$ fatty acid" refers to saturated and/or unsaturated carboxylic acids comprising $C_{10}$-$C_{18}$ fatty acids. In some embodiments, the term "$C_6$-$C_{24}$ fatty acid" refers to saturated and/or unsaturated carboxylic acids comprising $C_{12}$-$C_{16}$ fatty acids. In some embodiments, the term "$C_6$-$C_{24}$ fatty acid" refers to saturated and/or unsaturated carboxylic acids comprising $C_6$-$C_{24}$ fatty acids.

In some embodiments, the term "$C_6$-$C_{24}$ fatty acid" refers to saturated and/or unsaturated carboxylic acids comprising $C_{12}$-$C_{18}$ fatty acids.

In some embodiments, the term "$C_6$-$C_{24}$ fatty acid" refers to saturated and/or unsaturated carboxylic acids comprising about 90% of $C_8$-$C_{24}$ fatty acids. In some embodiments, the term "$C_6$-$C_{24}$ fatty acid" refers to saturated and/or unsaturated carboxylic acids comprising about 90% of $C_{10}$-$C_{22}$ fatty acids. In some embodiments, the term "$C_6$-$C_{24}$ fatty acid" refers to saturated and/or unsaturated carboxylic acids comprising about 90% of $C_8$-$C_{20}$ fatty acids. In some embodiments, the term "$C_6$-$C_{24}$ fatty acid" refers to saturated and/or unsaturated carboxylic acids comprising about 90% of $C_{10}$-$C_{18}$ fatty acids. In some embodiments, the term "$C_6$-$C_{24}$ fatty acid" refers to saturated and/or unsaturated carboxylic acids comprising about 90% of $C_6$-$C_{24}$ fatty acids. In some embodiments, the term "$C_6$-$C_{24}$ fatty acid" refers to saturated and/or unsaturated carboxylic acids comprising about 90% of $C_{12}$-$C_{18}$ fatty acids. In some embodiments, the term "$C_6$-$C_{24}$ fatty acid" refers to saturated and/or unsaturated carboxylic acids comprising about 90% of mixtures of $C_8$-$C_{24}$ fatty acids, $C_{10}$-$C_{22}$ fatty acids, $C_8$-$C_{20}$ fatty acids, $C_{10}$-$C_{18}$ fatty acids, $C_6$-$C_{24}$ fatty acids, and $C_{12}$-$C_{18}$ fatty acids.

In some embodiments, the term "$C_6$-$C_{24}$ fatty acid" refers to saturated and/or unsaturated carboxylic acids comprising greater than about 70%, 80% or 90% of $C_8$-$C_{24}$ fatty acid. In some embodiments, the term "$C_6$-$C_{24}$ fatty acid" refers to saturated and/or unsaturated carboxylic acids comprising greater than about 70%, 80% or 90% of $C_{10}$-$C_{22}$ fatty acid. In some embodiments, the term "$C_6$-$C_{24}$ fatty acid" refers to saturated and/or unsaturated carboxylic acids comprising greater than about 70%, 80% or 90% of $C_8$-$C_{20}$ fatty acid. In some embodiments, the term "$C_6$-$C_{24}$ fatty acid" refers to saturated and/or unsaturated carboxylic acids comprising greater than about 70%, 80% or 90% of $C_{10}$-$C_{18}$ fatty acid. In some embodiments, the term "$C_6$-$C_{24}$ fatty acid" refers to saturated and/or unsaturated carboxylic acids comprising greater than about 70%, 80% or 90% of $C_6$-$C_{24}$ fatty acid. In some embodiments, the term "$C_6$-$C_{24}$ fatty acid" refers to saturated and/or unsaturated carboxylic acids comprising greater than about 70%, 80% or 90% of $C_{12}$-$C_{18}$ fatty acid. In some embodiments, the term "$C_6$-$C_{24}$ fatty acid" refers to saturated and/or unsaturated carboxylic acids comprising greater than about 70%, 80% or 90% mixtures $C_8$-$C_{24}$ fatty acids, $C_{10}$-$C_{22}$ fatty acids, $C_8$-$C_{20}$ fatty acids, $C_{10}$-$C_{18}$ fatty acids, $C_6$-$C_{24}$ fatty acids, and $C_{12}$-$C_{18}$ fatty acids.

In some embodiments, the term "$C_6$-$C_{24}$ fatty acid" refers to saturated or unsaturated carboxylic acids comprising greater than about 50%, greater than about 60%, greater than about 70%, greater than about 80% or greater than about 90% of 6 carbon atoms. In some embodiments, the term "$C_6$-$C_{24}$ fatty acid" refers to saturated or unsaturated carboxylic acids comprising greater than about 50%, greater than about 60%, greater than about 70%, greater than about 80% or greater than about 90% of 8 carbon atoms. In some embodiments, the term "$C_6$-$C_{24}$ fatty acid" refers to saturated or unsaturated carboxylic acids comprising greater than about 50%, greater than about 60%, greater than about 70%, greater than about 80% or greater than about 90% of 10 carbon atoms. In some embodiments, the term "$C_6$-$C_{24}$ fatty acid" refers to saturated or unsaturated carboxylic acids comprising greater than about 50%, greater than about 60%, greater than about 70%, greater than about 80% or greater than about 90% of 12 carbon atoms. In some embodiments, the term "$C_6$-$C_{24}$ fatty acid" refers to saturated or unsaturated carboxylic acids comprising greater than about 50%, greater than about 60%, greater than about 70%, greater than about 80% or greater than about 90% of 14 carbon atoms. In some embodiments, the term "$C_6$-$C_{24}$ fatty acid" refers to saturated or unsaturated carboxylic acids comprising greater than about 50%, greater than about 60%, greater than about 70%, greater than about 80% or greater than about 90% of 16 carbon atoms. In some embodiments, the term "$C_6$-$C_{24}$ fatty acid" refers to saturated or unsaturated carboxylic acids comprising greater than about 50%, greater than about 60%, greater than about 70%, greater than about 80% or greater than about 90% of 18 carbon atoms. In some embodiments, the term "$C_6$-$C_{24}$ fatty acid" refers to saturated or unsaturated carboxylic acids comprising greater than about 50%, greater than about 60%, greater than about 70%, greater than about 80% or greater than about 90% of 20 carbon atoms. In some embodiments, the term "$C_6$-$C_{24}$ fatty acid" refers to saturated or unsaturated carboxylic acids comprising greater than about 50%, greater than about 60%, greater than about 70%, greater than about 80% or greater than about 90% of 22 carbon atoms. In some embodiments, the term "$C_6$-$C_{24}$ fatty acid" refers to saturated or unsaturated carboxylic acids comprising greater than about 50%, greater than about 60%, greater than about 70%, greater than about 80% or greater than about 90% of 24 carbon atoms. In some embodiments, the term "$C_6$-$C_{24}$ fatty acid" refers to saturated or unsaturated carboxylic acids comprising greater than about 50%, greater than about 60%, greater than about 70%, greater than about 80% or greater than about 90% of mixtures of 6 carbon atoms, 8 carbon atoms, 10 carbon atoms, 12 carbon atoms, 14 carbon atoms, 16 carbon atoms, 18 carbon atoms, 20 carbon atoms, 22 carbon atoms, and 24 carbon atoms.

In some embodiments, the term, "$C_6$-$C_{24}$ fatty acid" is selected from the group consisting of castor oil, cottonseed oil, olive oil, peanut oil, safflower oil, sesame oil, soybean oil, coconut oil, palm seed oil, and combinations thereof. In certain embodiments, the hydrophobic lipid is selected from the group consisting of glyceryl esters of castor oil, cottonseed oil, olive oil, peanut oil, safflower oil, sesame oil, soybean oil, coconut oil, palm seed oil, and combinations thereof.

In some embodiments, the hydrophilic organic compound comprises is selected from the group consisting of polyethylene glycol (including, but not limited to PEG100, PEG 200, PEG300, PEG 400, PEG 600), propylene glycol, glycerin, and dimethylsulfoxide. In certain embodiments, the hydrophilic organic compound comprises polyethylene glycol. In certain embodiments, the hydrophilic organic compound comprises propylene glycol.

The term "amphiphilic agent" as used herein refers to a molecule with affinity for both water and oil. These molecules are soluble or dispersible both in water and oil media, or improve the miscibility of one phase into the other phase. In some embodiments, the amphiphilic agent is selected from the group consisting of ethanol, benzyl alcohol, benzyl benzoate, N-methyl-2-pyrrolidone, and dimethylactamide. In some embodiments the amphiphilic agent is selected from sorbitan esters, polyethoxylated sorbitan esters, fatty alcohol ethoxylates, fatty acid ethoxylates, castor oil based ethoxylates, polyoxyethylene-polyoxypropylene block copolymers, propylene glycol diacetate, tyloxapol, Vitamin E TPGS and combinations thereof. In some embodiments, the amphiphilic agent is selected from the group consisting of polysorbate 20, polysorbate 40, polysorbate 60, polysorbate 65, and polysorbate 80. In some embodiments, the amphiphilic agent is one or more of polysorbate 20, polysorbate 40, polysorbate 60, polysorbate 65, and polysorbate 80. In some embodiments, the amphiphilic agent is selected from the group consisting of span 20, span 40, span 60, span 80, span 85 and span 120. In some embodiments, the amphiphilic agent is one or more of span 20, span 40, span 60, span 80, span 85 and span 120. In some embodiments the amphiphilic agent is selected from any combination of the group consisting of polysorbate 20, polysorbate 40, polysorbate 60, polysorbate 65, and polysorbate 80, span 20, span 40, span 60, span 80, span 85 and span 120.

The term "dispersed" as used herein refers to all means of establishing the presence of a beneficial agent in a composition according to the invention and includes a dispersion or suspension. The term "dispersion" refers to finely divided particles distributed in a carrier or dispersion medium. In general, the particulate (dispersed) phase and the carrier medium (continuous phase) may be solids, liquids, or gaseous, but unless stated differently or otherwise clear from the context of the discussion, dispersion as used herein refers to solid particles dispersed in a liquid vehicle.

The term "discrete particles" as used herein refers to particles of any shape having a $D_{90}$ particle size of about 0.5 μm to about 25 μm. In some embodiments, "discrete particles" as used herein refers to particles of any shape having a $D_{90}$ particle size of about 1.0 μm to about 25 μm. The term "particle size" as used herein refers to the median or the average dimension of particles in a sample and may be based on the number of particles, the volume of particles, or the mass of particles, and may be obtained using any number of standard measurement techniques known in the art. A desired particle size range material can be obtained directly from a synthesis process or any known particle size reduction processes can be used, such as but not limited to sifting, milling, micronization, fluid energy milling, media milling, ball milling, milled through high pressure homogenizer, air jet milling, and the like. Methods for determining $D_{10}$, $D_{50}$ and $D_{90}$ include laser light diffraction, such as using equipment from Malvern Instruments Ltd. (Malvern, Worcestershire, United Kingdom).

The terms "$D_{10}$," "$D_{50}$," and "$D_{90}$" indicating that, respectively, 10%, 50% and 90% of the distribution is below this value. For example, particles having a $D_{50}$ of about 10 μm have a median particle size of about 10 μm. A $D_{90}$ of about 15 μm indicates that 90% of the particles have a particle size of less than about 15 μm, and a $D_{10}$ of about 5 μm indicates that 10% of the particles have a particle size less than about 5 μm.

In some embodiments, the particles have a $D_{10}$ of about 5 μm. In some embodiments, the particles have a $D_{10}$ of about 4 μm. In some embodiments, the particles have a $D_{10}$ of about 3 μm. In some embodiments, the particles have a $D_{10}$ of about 2 μm. In some embodiments, the particles have a $D_{10}$ of about 1 μm. In some embodiments, the particles have a $D_{10}$ of about 0.5 μm. In some embodiments, the particles have a $D_{10}$ of about 0.2 μm. In some embodiments, the particles have a $D_{10}$ of about 0.1 μm. In some embodiments, the particles have a $D_{10}$ of about 0.005 μm. In some embodiments, the particles have a $D_{10}$ of about 0.005 μm to about 0.5 μm. In some embodiments, the particles have a $D_{10}$ of about 0.001 μm to about 4 μm. In some embodiments, the particles have a $D_{10}$ of about 0.1 μm to about 3 μm. In some embodiments, the particles have a $D_{10}$ of about 0.5 μm to about 2 μm. In some embodiments, the particles have a $D_{10}$ of about 0.8 μm to about 1 μm.

In some embodiments, the particles have a $D_{50}$ of about 20 μm. In some embodiments, the particles have a $D_{50}$ of about 15 μm. In some embodiments, the particles have a $D_{50}$ of about 12 μm. In some embodiments, the particles have a $D_{50}$ of about 10 μm. In some embodiments, the particles have a $D_{50}$ of about 9 μm. In some embodiments, the particles have a $D_{50}$ of about 8 μm. In some embodiments, the particles have a $D_{50}$ of about 7 μm. In some embodiments, the particles have a $D_{50}$ of about 6 μm. In some embodiments, the particles have a $D_{50}$ of about 5 μm. In some embodiments, the particles have a $D_{50}$ of about 4 μm. In some embodiments, the particles have a $D_{50}$ of about 3 μm. In some embodiments, the particles have a $D_{50}$ of about 2 μm. In some embodiments, the particles have a $D_{50}$ of about 1 μm. In some embodiments, the particles have a $D_{50}$ of about 0.5 μm. In some embodiments, the particles have a $D_{50}$ of about 0.4 μm. In some embodiments, the particles have a $D_{50}$ of about 0.3 μm. In some embodiments, the particles have a $D_{50}$ of about 0.2 μm. In some embodiments, the particles have a $D_{50}$ of about 0.1 μm. In some embodiments, the particles have a $D_{50}$ of about 0.005 μm. In some embodiments, the particles have a $D_{50}$ of about 0.005 μm to about 20 μm. In some embodiments, the particles have a $D_{50}$ of about 0.1 μm to about 15 μm. In some embodiments, the particles have a $D_{50}$ of between about 0.5 μm to about 10 μm. In some embodiments, the particles have a $D_{50}$ of about 0.8 μm to about 8 μm. In some embodiments, the particles have a $D_{50}$ of between about 1 μm to about 5 μm. In some embodiments, the particles have a $D_{50}$ of between about 2 μm to about 4 μm.

In some embodiments, the particles have a $D_{90}$ of about 25 μm. In some embodiments, the particles have a $D_{90}$ of about 20 μm. In some embodiments, the particles have a $D_{90}$ of about 15 μm. In some embodiments, the particles have a $D_{90}$ of about 10 μm. In some embodiments, the particles have a $D_{90}$ of about 9 μm. In some embodiments, the particles have a $D_{90}$ of about 8 μm. In some embodiments, the particles have a $D_{90}$ of about 7 μm. In some embodiments, the particles have a $D_{90}$ of about 6 μm. In some embodiments, the particles have a $D_{90}$ of about 5 μm. In some embodiments, the particles have a $D_{90}$ of about 4 μm. In some embodiments, the particles have a $D_{90}$ of about 3 μm. In some embodiments, the particles have a $D_{90}$ of about 2 μm. In some embodiments, the particles have a $D_{90}$ of about 1 μm. In some embodiments, the particles have a $D_{90}$ of about 0.5 μm. In some embodiments, the particles have a $D_{90}$ of about 0.2 μm. In some embodiments, the particles have a $D_{90}$ of about 0.1 μm. In some embodiments, the particles have a $D_{90}$ of about 0.005 μm. In some embodiments, the particles have a $D_{90}$ of about 0.5 μm to about 25 μm. In some embodiments, the particles have a $D_{90}$ of about 0.5 μm to about 15 μm. In some embodiments, the particles have a $D_{90}$ of about 0.5 μm to about 10 μm. In some embodiments, the particles have a $D_{90}$ of about 1 μm to about 20 μm. In some embodiments, the particles have a $D_{90}$ of about 1 μm to about 15 μm. In some embodiments, the particles have a $D_{90}$ of about 0.5 μm to about 10 μm. In some embodiments, the particles have a $D_{90}$ of between about 0.1 μm to about 7 μm. In some embodiments, the particles have a $D_{90}$ of between about 0.5 μm to about 5 μm. In some embodiments, the particles have a $D_{90}$ of between about 0.8 μm to about 2 μm.

The term "non-gelling" as used herein refers to a composition or formulation which is not in the form of a gel or a single phase and not thickened by the cross linking of polymers, or does not form a gel or a single phase and not thickened by the cross linking of polymers upon intramuscular or subcutaneous injection into a subject. Examples of non-gelling compositions include, for example, thickened solutions or suspensions, solutions or suspensions with thixotropic property, and the like. The term "thickened," as used herein refers to compositions in which the viscosity has been enhanced to a viscosity greater than about that of the vehicle at ambient room temperature.

Previously known oil-based formulations comprised a drug solubilized in the oil, instead of a suspension of drug in an oil. Applicants have found that by using a poorly soluble drug, in combination with a non-aqueous liquid vehicle (e.g., an oil) and an amphiphilic agent, wherein the drug is dispersed as discrete particles as described herein, that a less viscous formulation can be achieved suitable for use as an injectable. Applicants have also surprisingly found that the injectable formulations described in the disclosure can obtain acceptable bioavailability of the drug in the blood stream of a subject, even though the drug particles may be coated with a non-water miscible oil. Surprisingly, the formulations of the present disclosure provide a means of injectability of drug products as suspensions that offer good systemic exposure, and long acting performance without ill effects on the subjects.

The term "thixotropic" as used herein refers to that property of a formulation which causes it to behave as a free flowing liquid under shear conditions, i.e., the formulation flows faster than it does when not under shear conditions or at least exhibits a decrease in apparent viscosity upon application of mechanical force such as shear force. The extent of the reduction is in part a function of the shear rate of the formulation when subjected to the shearing force. When the shearing force is removed, the viscosity of the thixotropic formulation returns to a viscosity at or near that which it displayed prior to being subjected to the shearing force. Accordingly, a thixotropic formulation may be subjected to a shearing force when injected from a syringe which temporarily reduces its viscosity during the injection process. When the injection process is completed, the shearing force is removed and the formulation returns very near to its previous state. For example, at rest (i.e., less than or equal to about 0.1/s shear rate), the viscosity of the formulation is greater than about 15 poise to about 300 poise at about 25° C. At higher stresses (about 100/s shear rate), the viscosity tend to be about 0.5 poise to about 4 poise at about 25° C.

The term "viscosity" as used herein refers to the resistance of a fluid to flow due to a shearing force. For example, a fluid with a high viscosity will flow more slowly than a fluid with a low viscosity. In some embodiments, the formulation of the present invention includes a viscosity of less than about 300 poise at a shear rate of 0.1/s at 25° C. In some embodiments, the formulation of the present invention includes a viscosity of less than about 275 poise at a shear rate of 0.1/s at 25° C. In some embodiments, the formulation of the present invention includes a viscosity of less than about 250 poise at a shear rate of 0.1/s at 25° C. In some embodiments, the formulation of the present invention includes a viscosity of less than about 225 poise at a shear rate of 0.1/s at 25° C. In some embodiments, the formulation of the present invention includes a viscosity of less than about 200 poise at a shear rate of 0.1/s at 25° C. In some embodiments, the formulation of the present invention includes a viscosity of less than about 175 poise at a shear rate of 0.1/s at 25° C. In some embodiments, the formulation of the present invention includes a viscosity of less than about 150 poise at a shear rate of 0.1/s at 25° C. In some embodiments, the formulation of the present invention includes a viscosity of about 150 poise to about 300 poise at a shear rate of 0.1/s at 25° C. In some embodiments, the formulation of the present invention includes a viscosity of about 175 poise to about 275 poise at a shear rate of 0.1/s at 25° C. In some embodiments, the formulation of the present invention includes a viscosity of about 150 poise to about 250 poise at a shear rate of 0.1/s at 25° C. In some embodiments, the formulation of the present invention includes a viscosity of about 100 poise to about 200 poise at a shear rate of 0.1/s at 25° C.

In some embodiments, the formulation of the present invention includes a viscosity of less than about 150 poise at a shear rate of 0.25/s at 25° C. In some embodiments, the formulation of the present invention includes a viscosity of less than about 125 poise at a shear rate of 0.25/s at 25° C. In some embodiments, the formulation of the present invention includes a viscosity of less than about 100 poise at a shear rate of 0.25/s at 25° C. In some embodiments, the formulation of the present invention includes a viscosity of less than about 75 poise at a shear rate of 0.25/s at 25° C. In some embodiments, the formulation of the present invention includes a viscosity of about 75 poise to about 150 poise at a shear rate of 0.25/s at 25° C. In some embodiments, the formulation of the present invention includes a viscosity of about 100 poise to about 125 poise at a shear rate of 0.25/s at 25° C. In some embodiments, the formulation of the present invention includes a viscosity of about 150 poise to about 200 poise at a shear rate of 0.25/s at 25° C.

In some embodiments, the formulation of the present invention includes a viscosity of less than about 50 poise at a shear rate of 1/s at 25° C. In some embodiments, the formulation of the present invention includes a viscosity of less than about 45 poise at a shear rate of 1/s at 25° C. In some embodiments, the formulation of the present invention includes a viscosity of less than about 40 poise at a shear rate of 1/s at 25° C. In some embodiments, the formulation of the present invention includes a viscosity of less than about 35 poise at a shear rate of 1/s at 25° C. In some embodiments, the formulation of the present invention includes a viscosity of less than about 30 poise at a shear rate of 1/s at 25° C. In some embodiments, the formulation of the present invention includes a viscosity of less than about 25 poise at a shear rate of 1/s at 25° C. In some embodiments, the formulation of the present invention includes a viscosity of about 25 poise to about 50 poise at a shear rate of 1/s at 25° C. In some embodiments, the formulation of the present invention includes a viscosity of about 30 poise to about 45 poise at a shear rate of 1/s at 25° C. In some embodiments, the formulation of the present invention includes a viscosity of about 35 poise to about 40 poise at a shear rate of 1/s at 25° C.

In some embodiments, the formulation of the present invention includes a viscosity of less than about 10 poise at a shear rate of 10/s at 25° C. In some embodiments, the formulation of the present invention includes a viscosity of less than about 9 poise at a shear rate of 10/s at 25° C. In some embodiments, the formulation of the present invention includes a viscosity of less than about 8 poise at a shear rate of 10/s at 25° C. In some embodiments, the formulation of the present invention includes a viscosity of less than about 7 poise at a shear rate of 10/s at 25° C. In some embodiments, the formulation of the present invention includes a viscosity of less than about 6 poise at a shear rate of 10/s at 25° C. In some embodiments, the formulation of the present invention includes a viscosity of less than about 5 poise at a shear rate of 10/s at 25° C. In some embodiments, the formulation of the present invention includes a viscosity of about 5 poise to about 10 poise at a shear rate of 10/s at 25° C. In some embodiments, the formulation of the present invention includes a viscosity of about 6 poise to about 9 poise at a shear rate of 10/s at 25° C. In some embodiments, the formulation of the present invention includes a viscosity of about 7 poise to about 8 poise at a shear rate of 10/s at 25° C.

In some embodiments, the formulation of the present invention includes a viscosity of less than about 4 poise at a shear rate of 100/s at 25° C. In some embodiments, the formulation of the present invention includes a viscosity of less than about 3 poise at a shear rate of 100/s at 25° C. In some embodiments, the formulation of the present invention includes a viscosity of less than about 2 poise at a shear rate of 100/s at 25° C. In some embodiments, the formulation of the present invention includes a viscosity of less than about 1 poise at a shear rate of 100/s at 25° C. In some embodiments, the formulation of the present invention includes a viscosity of about 1 poise to about 4 poise at a shear rate of 100/s at 25° C. In some embodiments, the formulation of the present invention includes a viscosity of about 2 poise to about 3 poise at a shear rate of 100/s at 25° C.

In some embodiments, the formulation of the present invention includes a viscosity of less than about 2 poise at a shear rate of 500/s at 25° C. In some embodiments, the formulation of the present invention includes a viscosity of less than about 1.5 poise at a shear rate of 500/s at 25° C. In some embodiments, the formulation of the present invention includes a viscosity of less than about 1.0 poise at a shear rate of 500/s at 25° C. In some embodiments, the formulation of the present invention includes a viscosity of less than about 0.5 poise at a shear rate of 500/s at 25° C. In some embodiments, the formulation of the present invention includes a viscosity of less than about 0.25 poise at a shear rate of 500/s at 25° C. In some embodiments, the formulation of the present invention includes a viscosity of about 0.25 poise to about 2 poise at a shear rate of 500/s at 25° C. In some embodiments, the formulation of the present invention includes a viscosity of about 0.5 poise to about 1.5 poise at a shear rate of 500/s at 25° C.

The terms "treating", "treatment" and the like, as used herein, shall include the management and care of a subject or patient (preferably a mammal, more preferably a human) for the purpose of combating a disease, condition, or disorder and includes the administration of the formulation described herein to prevent the onset of the symptoms or complications, alleviate the symptoms or complications, or eliminate the disease, condition, or disorder.

The term "therapeutically effective amount" or "effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following: (1) preventing a disease, condition or disorder in an individual that may be predisposed to the disease, condition or disorder but does not yet experience or display the pathology or symptomatology of the disease, (2) treating a disease, condition or disorder in an individual that is experiencing or displaying the pathology or symptomatology of the disease, condition or disorder (i.e., arresting further development of the pathology and/or symptomatology), and (3) mitigating a disease, condition or disorder in an individual that is experiencing or displaying the pathology or symptomatology of the disease, condition or disorder (i.e., reversing the pathology and/or symptomatology). The amount of an active ingredient that is "effective" may vary from individual to individual, depending on the age, weight, general condition, and other factors of the individual, or depending on the type and severity of the disorder or disease being treated. An appropriate "effective" amount in any individual may be determined by one of ordinary skill in the art using routine experimentation.

The term "excipient" refers to a component of a pharmaceutical product that is not an active ingredient such as, vehicles, diluents, binders, thickening agent, anti-adherents, wetting agents, deflocculating agents, tonicity adjusting agents, buffering agents, antioxidants, preservatives, stabilizers, release controlling agents, and other excipients known to the person skilled in the art. The pharmaceutical excipients that are useful in preparing a formulation as disclosed herein, for example, are generally safe and non-toxic for purposes of injecting into the body subcutaneously and/or intramuscularly.

The term "syringe" refers to cartridges, injection "pens," and other types of barrels or reservoirs adapted to be assembled with one or more other components to provide a functional syringe. "Syringe" is also broadly defined to include related articles such as auto-injectors, which provide a mechanism for dispensing the contents.

The term "vial" refers to any walled container, whether rigid or solid, of any shape or size, designed to hold a solution or suspension, such as a therapeutic agent solution or suspension and dispense the solution or suspension in a required device.

The term "administering" refers to introducing a substance into a subject. In general, any route of administration may be utilized including, for example, parenteral (e.g., intravenous), subcutaneous, peritoneal, intra-arterial, inhalation, introduction into the cerebrospinal fluid, or instillation into body compartments. In some embodiments, administration is intramuscular. Additionally or alternatively, in some embodiments, administration is subcutaneous.

Generally, the invention disclosed herein relates to long acting injectable formulations of poorly water-soluble active pharmaceutical ingredients.

In some embodiments, the invention is directed to a long acting injectable formulation comprising: (i) a poorly water-soluble active pharmaceutical ingredient; (ii) a non-aqueous liquid vehicle comprising (a) a hydrophobic lipid, and/or (b) a hydrophilic organic compound, and (iii) an amphiphilic agent.

In some embodiments, the poorly water-soluble active pharmaceutical ingredient is about 1% to about 50% (by weight) of the formulation, about 2% to about 40% (by weight) of the formulation, about 3% to about 30% (by weight) of the formulation, about 4% to about 40% (by weight) of the formulation or about 5% to about 20% (by weight) of the formulation. In some embodiments, the poorly water-soluble API is about 5%, 6%, 7%, 8%, 9%, 10%, 11%, 12%, 13%, 14%, 15%, 20%, 25% or 30% (by weight) of the formulation.

In some embodiments, the hydrophobic lipid is about 40% to about 99% (by weight) of the formulation, about 50% to about 97% (by weight) of the formulation, about 60% to about 95% (by weight) of the formulation, about 70% to about 93% (by weight) of the formulation or about 80% to about 91% (by weight) of the formulation. In some embodiments, the hydrophobic lipid is about 80%, 85%, 90%, 91%, 92%, 93%, 94%, 95%, 96%, 97%, 98%, 99%, or 99.5% (by weight) of the formulation.

In some embodiments, the hydrophilic organic compound is about 40% to about 99% (by weight) of the formulation, about 50% to about 97% (by weight) of the formulation, about 60% to about 95% (by weight) of the formulation, about 70% to about 93% (by weight) of the formulation or about 80% to about 91% (by weight) of the formulation. In some embodiments, the hydrophilic organic compound is about 80%, 85%, 90%, 91%, 92%, 93%, 94%, 95%, 96%, 97%, 98%, 99%, or 99.5% (by weight) of the formulation.

In some embodiments, the amphiphilic agent is about 0.1% to about 50% (by weight) of the formulation, 0.5% to about 50% (by weight) of the formulation, about 1% to about 30% (by weight) of the formulation, about 2% to about 20% (by weight) of the formulation, about 3% to about 15% (by weight) of the formulation or about 5% to about 10% (by weight) of the formulation. In some embodiments, the amphiphilic agent is about 5%, 6%, 7%, 8%, 9%, 10%, 11%, 12%, 13%, 14%, 15%, 16%, or 20% (by weight) of the formulation.

In some embodiments, the invention is directed to a long acting injectable formulation comprising: (i) a poorly water-soluble active pharmaceutical ingredient in an amount of about 1% to about 50% by weight of the dosage form; (ii) a non-aqueous liquid vehicle in an amount of about 40% to about 99% by weight of the dosage form comprising (a) a hydrophobic lipid, (b) a hydrophilic organic compound, or a combination of (a) and (b); and (iii) an amphiphilic agent in an amount of about 0.1% to about 50% by weight of the dosage form.

In some embodiments, the invention is directed to a long acting injectable formulation comprising: (i) a poorly water-soluble active pharmaceutical ingredient in an amount of about 1% to about 50% by weight of the dosage form; (ii) a non-aqueous liquid vehicle in an amount of about 40% to about 99% by weight of the dosage form comprising (a) a hydrophobic lipid, (b) a hydrophilic organic compound, or a combination of (a) and (b); and (iii) an amphiphilic agent in an amount of about 0.1% to about 50% by weight of the dosage form.

In some embodiments, the invention is directed to a long acting injectable formulation comprising: (i) a poorly water-soluble active pharmaceutical ingredient in an amount of about 1% to about 50% by weight of the dosage form; (ii) a non-aqueous hydrophobic lipid vehicle in an amount of about 40% to about 99% by weight of the dosage form; and (iii) an amphiphilic agent in an amount of about 0.1% to about 50% by weight of the dosage form.

In some embodiments, the invention is directed to a long acting injectable formulation comprising: (i) a poorly water-soluble active pharmaceutical ingredient in an amount of about 1% to about 50% by weight of the dosage form; (ii) a hydrophilic organic compound in an amount of about 40% to about 99% by weight of the dosage form; and (iii) an amphiphilic agent in an amount of about 0.1% to about 50% by weight of the dosage form.

In some embodiments, the poorly water-soluble active pharmaceutical ingredient is an anti-psychotic drug selected from the group consisting of free base, salt or ester of lurasidone, aripiprazole, asenapine, iloperidone, olanzapine, paliperidone, risperidone, ziprasidone, cariprazine, brexpiprazole, vortioxetine, vilazodone, duloxentine, and mirtazapine. In certain embodiments, the poorly water-soluble active pharmaceutical ingredient is free base or salt of ziprasidone. In certain embodiments, the poorly water-soluble active pharmaceutical ingredient is free base or salt of lurasidone. In certain embodiments, the poorly water-soluble active pharmaceutical ingredient is lurasidone hydrochloride. In certain embodiments, the poorly water-soluble active pharmaceutical ingredient is ziprasidone hydrochloride. In certain embodiments, the poorly water-soluble active pharmaceutical ingredient is free base or salt of cariprazine. In certain embodiments, the poorly water-soluble active pharmaceutical ingredient is a free base, salt or ester of brexpiprazole.

In some embodiments, the amphiphilic agent comprises one or more agents selected from the group consisting of ethanol, benzyl alcohol, benzyl benzoate, N-methyl-2-pyrrolidone, dimethylactamide, sorbitan esters, polyethoxylated sorbitan esters, fatty alcohol ethoxylates, fatty acid ethoxylates, castor oil based ethoxylates, polyoxyethylene-polyoxypropylene block copolymers, Vitamin E TPGS, and combinations thereof. In certain embodiments, the amphiphilic agent comprises polysorbate 20 and span 80. In certain embodiments, the amphiphilic agent comprises polysorbate 20. In certain embodiments, the amphiphilic agent comprises span 80.

In some embodiments, the vehicle comprises one or more amphiphilic agents selected from the group consisting of ethanol, benzyl alcohol, benzyl benzoate, N-methyl-2-pyrrolidone, dimethylacetamide, sorbitan esters, polyethoxylated sorbitan esters, fatty alcohol ethoxylates, fatty acid ethoxylates, castor oil based ethoxylates, polyoxyethylene-polyoxypropylene block copolymers, and combinations thereof.

In some embodiments, the non-aqueous hydrophobic lipid vehicle and/or the hydrophilic organic compound further comprises one or more preservatives. In certain embodiments, the preservative is selected from the group consisting of benzyl alcohol, benzyl benzoate, butylated hydroxyltoluene (BHT), butylated hydroxyanisole (BHA), propyl gallate, methylparaben, propylparaben, tocopherols, and combinations thereof.

In some embodiments, the formulation exhibits a thixotropy, specifically, to achieve high viscosity at storage providing physical stability of the suspended drug particles as well as lower viscosity upon shaking and injecting to provide ease of administration through a relatively narrow hypodermic needle, minimizing patient discomfort.

In some embodiments, the formulation has a viscosity of less than 10 poise at a shear rate of 10/s at 25° C. In certain embodiments, the formulation has a viscosity of about 0.5 poise to about 50 poise at a shear rate of 1/s at 25° C. In certain embodiments, the formulation has a viscosity of about 0.5 poise to about 10 poise at a shear rate of 10/s at 25° C. In certain embodiments, the formulation has a viscosity of about 0.5 poise to about 4 poise at 100/s shear rate at 25° C.

In some embodiments, the present invention is directed to a long acting injectable formulation comprising: (i) about 1% to about 50% of lurasidone as free base or salt; (ii) about 40% to about 99% of a vehicle comprising a hydrophobic lipid comprising a glyceryl ester of a $C_6$-$C_{24}$ fatty acid; and (iii) about 0.5% to about 50% of an amphiphilic agent, wherein the lurasidone is dispersed as discrete particles having a $D_{90}$ particle size of about 0.5 μm to about 25 μm in the vehicle, and wherein the formulation is non-gelling and thixotropic with a viscosity of less than 10 poise at a shear rate of 10/s at 25° C.

In some embodiments, the present invention is directed to a long acting injectable formulation comprising: (i) about 1% to about 50% of lurasidone as free base or salt; (ii) about 40% to about 99% of a vehicle comprising a hydrophobic lipid comprising a glyceryl ester of a $C_6$-$C_{24}$ fatty acid; and (iii) about 1% to about 50% of an amphiphilic agent, wherein the lurasidone is dispersed as discrete particles having a $D_{90}$ particle size of about 0.5 μm to about 25 μm in the vehicle, and wherein the formulation is non-gelling and thixotropic with a viscosity of less than 10 poise at a shear rate of 10/s at 25° C.

In some embodiments, the non-aqueous hydrophobic lipid is sesame oil.

In some embodiments, the amphiphilic agent is sorbitan monooleate.

In some embodiments, the present invention is directed to a long acting injectable formulation comprising: (i) about 1% to about 50% of lurasidone as free base or salt; (ii) about 40% to about 99% of a vehicle comprising a hydrophilic organic compound comprising polyethylene glycol or propylene glycol; and (iii) about 0.5% to about 50% of an amphiphilic agent, wherein the lurasidone is dispersed as discrete particles having a $D_{90}$ particle size of about 0.5 μm to about 25 μm in the vehicle, and wherein the formulation is non-gelling and thixotropic with a viscosity of less than 10 poise at a shear rate of 10/s at 25° C.

In some embodiments, the present invention is directed to a long acting injectable formulation comprising: (i) about 1% to about 50% of lurasidone as free base or salt; (ii) about 40% to about 99% of a vehicle comprising a hydrophilic organic compound comprising polyethylene glycol or propylene glycol; and (iii) about 1% to about 50% of an amphiphilic agent, wherein the lurasidone is dispersed as discrete particles having a $D_{90}$ particle size of about 0.5 μm to about 25 μm in the vehicle, and wherein the formulation is non-gelling and thixotropic with a viscosity of less than 10 poise at a shear rate of 10/s at 25° C.

In some embodiments, the amphiphilic agent is polyethoxylated sorbitan esters.

In some embodiments, the hydrophilic organic compound comprises polyethylene glycol or propylene glycol.

In some embodiments, the present invention is directed to a long acting injectable formulation comprising: (i) about 1% to about 50% of lurasidone as free base or salt; (ii) about 40% to about 99% of a non-aqueous liquid vehicle, comprising: (a) a hydrophobic lipid comprising a glyceryl ester of a $C_6$-$C_{24}$ fatty acid, (b) a hydrophilic organic compound selected from the group consisting of polyethylene glycol, propylene glycol, glycerin, and dimethylsulfoxide, or a combination of (a) and (b); and (iii) about 0.1% to about 50% of an amphiphilic agent, wherein the lurasidone is dispersed as discrete particles having a $D_{90}$ particle size of about 0.5 μm to about 25 μm in the vehicle, and wherein the formulation is non-gelling and thixotropic with a viscosity of less than 10 poise at a shear rate of 10/s at 25° C.

In some embodiments, the non-aqueous hydrophobic lipid is sesame oil.

In some embodiments, the hydrophilic organic compound is polyethylene glycol.

In some embodiments, the invention is directed to a process for preparing a long acting injectable formulation, comprising: (i) mixing an amphiphilic agent with a non-aqueous liquid vehicle comprising (a) a hydrophobic lipid comprising a glyceryl ester of a $C_6$-$C_{24}$ fatty acid, (b) a hydrophilic organic compound selected from the group consisting of polyethylene glycol, propylene glycol, glycerin, and dimethylsulfoxide, or a combination of (a) and (b); (ii) dispersing a poorly water-soluble active pharmaceutical ingredient in the mixture of (i) and mixing to form a dispersion; and (iii) milling the dispersion of (ii) to achieve an active pharmaceutical ingredient having a $D_{90}$ particle size of about 0.5 μm to about 25 μm to obtain the long acting injectable formulation.

In some embodiments, the invention is directed to a process for preparing a long acting injectable formulation, comprising: (i) mixing an amphiphilic agent with a non-aqueous liquid vehicle comprising (a) a hydrophobic lipid comprising a glyceryl ester of a $C_6$-$C_{24}$ fatty acid; (b) a hydrophilic organic compound selected from the group consisting of polyethylene glycol, propylene glycol, glycerin, and dimethylsulfoxide, or a combination of (a) and (b); and (ii) dispersing a poorly water-soluble active pharmaceutical ingredient having a $D_{90}$ particle size of about 0.5 μm to about 25 μm in the mixture of (i) and mixing to form a uniform dispersion to obtain the long acting injectable formulation.

In some embodiments, the process for preparing a long acting injectable formulation further comprises adding additional excipients to form a final dosage form.

In some embodiments, the invention is directed to a process for preparing a long acting injectable formulation, wherein the active pharmaceutical ingredient is an antipsychotic drug selected from the group consisting of free base, salt or ester of lurasidone, aripiprazole, asenapine, iloperidone, olanzapine, paliperidone, risperidone, ziprasidone, cariprazin, brexpiprazole, vortioxetine, vilazodone, duloxentine, and mirtazapine.

In some embodiments, the invention is directed to a process for preparing a long acting injectable formulation of a free base or salt of lurasidone. In some embodiments, the invention is directed to a process for preparing a long acting injectable formulation of a free base or salt of cariprazine. In some embodiments, the invention is directed to a process for preparing a long acting injectable formulation of a free base, salt or ester of brexpiprazole.

In some embodiments, the invention is directed to an injectable pharmaceutical dosage form, comprising (i) a long acting injectable formulation as described herein, and (ii) a pre-filled syringe or vial.

In some embodiments, the invention is directed to a method of administering a long acting injectable formulation intramuscularly or subcutaneously as described herein.

In some embodiments, the invention is directed to a method of administering a long acting injectable formulation intramuscularly or subcutaneously as described herein once a week.

In some embodiments of the present invention, the invention is directed to administering the formulations described herein to a subject, e.g., a human or domesticated animal subject. In some embodiments, administration can occur daily, weekly, biweekly, monthly, or bi monthly. In some embodiments, the invention is directed to a method of administering a long acting injectable formulation intramuscularly or subcutaneously as described herein once a week, or once a month. In some embodiments, the invention is directed to a method of administering a long acting injectable formulation intramuscularly or subcutaneously as described herein once every three months.

In some embodiments, the invention is directed to a method of treating a psychotic disorder, the method comprising administering intramuscularly or subcutaneously a long acting injectable formulation as described herein.

In some embodiments, the invention is directed to a method of treating a psychotic disorder, the method comprising administering intramuscularly or subcutaneously a long acting injectable formulation as described herein once a week.

In some embodiments, the invention is directed to a method of treating a psychotic disorder, the method comprising administering intramuscularly or subcutaneously a long acting injectable formulation as described herein once a month. In some embodiments, the invention is directed to a method of treating a psychotic disorder, the method comprising administering intramuscularly or subcutaneously a long acting injectable formulation as described herein once every three months.

The present invention has been described by way of example only, and it is to be recognized that modifications thereto which fall within the scope and spirit of the appended claims, and which would be obvious to a skilled person based upon the disclosure herein, are also considered to be included within the invention.

EXAMPLES

Example—1

Latuda® Lurasidone HCl Immediate-release Tablets marketed in the U.S. contains lurasidone as a hydrochloride salt. An initial attempt was made to prepare an aqueous-based long acting formulation of lurasidone HCl. An aqueous dispersion of lurasidone HCl in an aqueous solution of an amphiphilic agent of polyethoxylated sorbitan esters (Polysorbate 20), in a composition listed in Table 1, was milled using a wet milling process of ball milling (DYNO®-MILL, Type KDL Special, manufactured by Basel, Switzerland).

TABLE 1

| Ingredient | mg per Dose |
|---|---|
| Lurasidone Hydrochloride | 300.0 |
| Polysorbate 20 | 30.00 |
| Water for injection | q.s. 3.0 mL |
| Total | 3.0 mL |

The pH of the dispersion was 3.1 prior to the wet milling process and 2.9 after milling. The acidic nature of this aqueous-based long acting formulation of lurasidone HCl can lead to irritation and possible tissue damage at the injection site, and hence is not suitable for administration in patients in need thereof. Additionally, lurasidone particle size growth and changes in the particle size distribution, as well as time-dependent physical instability was observed for this aqueous-based long acting formulation of lurasidone HCl.

It is known that lurasidone displays a pH dependent solubility profile with a lower solubility at higher pH values. An attempt was made to mill the lurasidone HCl API in aqueous media buffered to pH 7 with a phosphate buffer and sodium hydroxide. Despite stabilization of pH with buffering agents, during milling, the pH dropped from pH 7 to pH 6. The pH of the aqueous dispersion was subsequently readjusted to pH 7 with sodium hydroxide after the milling process.

While the suspension, adjusted to pH 7, was milled to attain the desired particle size distribution using a wet milling process of a ball mill, the osmolarity of the resulting suspension was significantly high (~1000 Osmol/L) due to the addition of sodium hydroxide for the pH adjustment from 6 to 7. An aqueous system with such high osmolarity is not suitable for injection. Injectable products typically have osmolarity values between 250 Osmol/L to 350 Osmol/L. Therefore, an aqueous-based vehicle is not feasible for a long acting formulation of lurasidone HCl.

Surprisingly, the inventors have discovered that the milled lurasidone dispersed as discrete particles in a non-aqueous liquid vehicle comprising (a) a hydrophobic lipid comprising a glyceryl ester of a $C_6$-$C_{24}$ fatty acid, or (b) a hydrophilic organic compound selected from the group consisting of polyethylene glycol, propylene glycol, glycerin, and dimethylsulfoxide, forms a suspension with a stabilized particle size distribution and exhibited sustained release phenomenon (See Examples 2 to 5.)

A non-aqueous hydrophobic or hydrophilic vehicle-based long acting injectable suspension of lurasidone hydrochloride overcame the limitation of instability (crystal growth) of an aqueous-based lurasidone HCl long acting formulation. This non-aqueous hydrophobic or hydrophilic vehicle-based lurasidone hydrochloride long acting formulation can provide a long acting lurasidone formulation for patients with psychopathological symptoms. Currently, there is no long acting injectable lipid-based suspension of lurasidone HCL or other antipsychotic drugs available in the market. Availability of a long acting injectable formulation of this drug as described herein may be desirable for physicians and patients in need of lurasidone to manage the schizophrenia and bipolar syndrome.

As shown in FIG. 1, in a representative embodiment of the present invention, the injectable dosage form includes (a) an active pharmaceutical ingredient ("API"), lurasidone as a free base, a salt, an ester or a mixture thereof; (b) a hydrophobic lipid vehicle comprising glyceryl esters of fatty acids and an amphiphilic agent. FIG. 1 provides a typical method for making representative dosage forms according to the present invention, wherein lurasidone API was mixed with a hydrophobic lipid vehicle in combination with an amphiphilic agent. The lurasidone dispersion was then milled using a wet milling process of a ball mill or high shear mill, or a high pressure homogenizer, to obtain particles with a $D_{90}$ particle size of about 0.5 μm to about 25 μm.

The milled suspension in the hydrophobic lipid vehicle was stable with no change in assay and impurity levels. The particles thus obtained were suspended in the hydrophobic lipid vehicle with minimal or no sedimentation. The formulation was easily redispersable with minor shaking and no growth of milled particles was observed. The viscosity was 2.65 poise at 10/s shear rate.

The drug release in-vivo was tailored by controlling the particle size of suspension by adjusting milling conditions, including but not limited to number of passes, bead size, bead material, bead load, dispersion load, motor tip speed, viscosity of the media, suspension flow rate, and the temperature of the ball mill, or the pressure and aperture of the change parts in the high pressure homogenizer. The in vivo drug release was also controlled by the viscosity of the suspension. The viscosity of the suspension was tailored through combination of sesame oil with various hydrophobic lipids which include, but are not limited to, castor oil, cottonseed oil, corn oil, and peanut oil.

High-Performance Liquid Chromatography Method for Drug Content Assay: Lurasidone HCl drug content in the suspension was determined by reverse-phase (RP)-HPLC using a Kinetex XB-C18, 100 mm×4.60 mm, 2.6 μm column (Phenomenex). An isocratic elution method was used with mixture of 0.4% trifluoroacetic acid and acetonitrile (60/40, v/v) with a flow rate of 1.0 mL/min and 10 μL of injection volume at ambient column temperature. UV absorbance was measured at 230 nm. The generated concentration values were subsequently used to calculate actual drug-load values.

High-Performance Liquid Chromatography Method for Related Substances: Related Substances of lurasidone HCl in the suspension were determined by reverse-phase (RP)-HPLC using a Kinetex XB-C18, 100 mm×4.60 mm, 2.6 μm column (Phenomenex). A gradient elution method was used with mobile phase A (0.1% [v/v] phosphoric acid in water) and mobile phase B (100% acetonitrile). The gradient was 85:15 (A:B) to 25:75 (A:B) over 35 minutes, with a flow rate of 1.0 mL/min and 10 μL of injection volume at ambient column temperature. UV absorbance was measured at 230 nm. Individual % known and % unknown related compounds in the suspension were quantitated against an external standard as a % w/w.

Particle Size Characterization of a Long Acting Injectable Formulation of Lurasidone in a Non-Aqueous Hydrophobic Lipid Vehicle:

The particle size distributions of oily based suspensions of lurasidone were measured using a Malvern Mastersizer 2000 Particle Size Distribution Analyzer with sunflower seed oil as dispersant. Average particle sizes were reported in micrometers at $D_{10}$, $D_{50}$, and $D_{90}$. ($D_{XX}$ is defined as the diameter at which XX % of the particle population lays below that size) The suspension was characterized further for specific surface area ($m^2/g$), surface weighted mean (SWM) (μm) and volume weighed mean (VWM) (μm).

Particle Size Characterization of a Long Acting Injectable Formulation of Lurasidone in a Hydrophilic Organic Compound:

The particle size distributions of aqueous-based suspensions of lurasidone were measured using a Malvern Mastersizer 2000 Particle Size Distribution Analyzer with a saturated solution of lurasidone in water used as dispersant. The suspension was characterized further for specific surface area (m2/g), surface weighted mean (SWM) (μm) and volume weighed mean (VWM) (μm).

Viscosity Measurements:

Viscosity was determined between 0.1/s to 500/s shear rates at 25° C. using an AR-G2 rheometer equipped with 40 mm parallel plate geometry and peltier plate to control the temperature.

Texture Analysis Measurements for Syringeability Data:

Syringeability of suspension was measured using a TA.x2i Texture Analyzer. For analysis, the suspension was filled in 5 mL neutral glass (Type I) barrels with a polystyrene plunger rod. The plunger was depressed at a pre-test speed of 3.00 mm/sec and at a variable test speed during the test. The force (N) and time (sec) required to inject 5 mL of suspension was measured.

Example—2

A long acting injectable formulation of lurasidone in a non-aqueous hydrophobic lipid vehicle was prepared using a wet milling process of ball/media milling via DYNO®-MILL (Type KDL Special, manufactured by Basel, Switzerland).

The ingredients, as shown in Table 2, were added to a stainless steel vessel to form a dispersion.

TABLE 2

| Ingredient | mg per Dose |
|---|---|
| Lurasidone hydrochloride | 300.0 |
| Sorbitan monooleate | 30.00 |
| Sesame oil | q.s. to 3 mL |
| Total | 3 mL |

The grinding chamber was filled to 80% capacity with yttrium-stabilized zirconium oxide beads, and the dispersion was passed through the mill operating at the conditions highlighted in Table 3:

TABLE 3

| Grinding chamber | Water-cooled jacketed 0.3 L Chamber |
|---|---|
| Motor tip speed | 10 meters/sec |
| Grinding medium | 240 mL of yttrium stabilized zirconium oxide beads |
| Suspension flow rate | 140 g/min |

Figure 2:
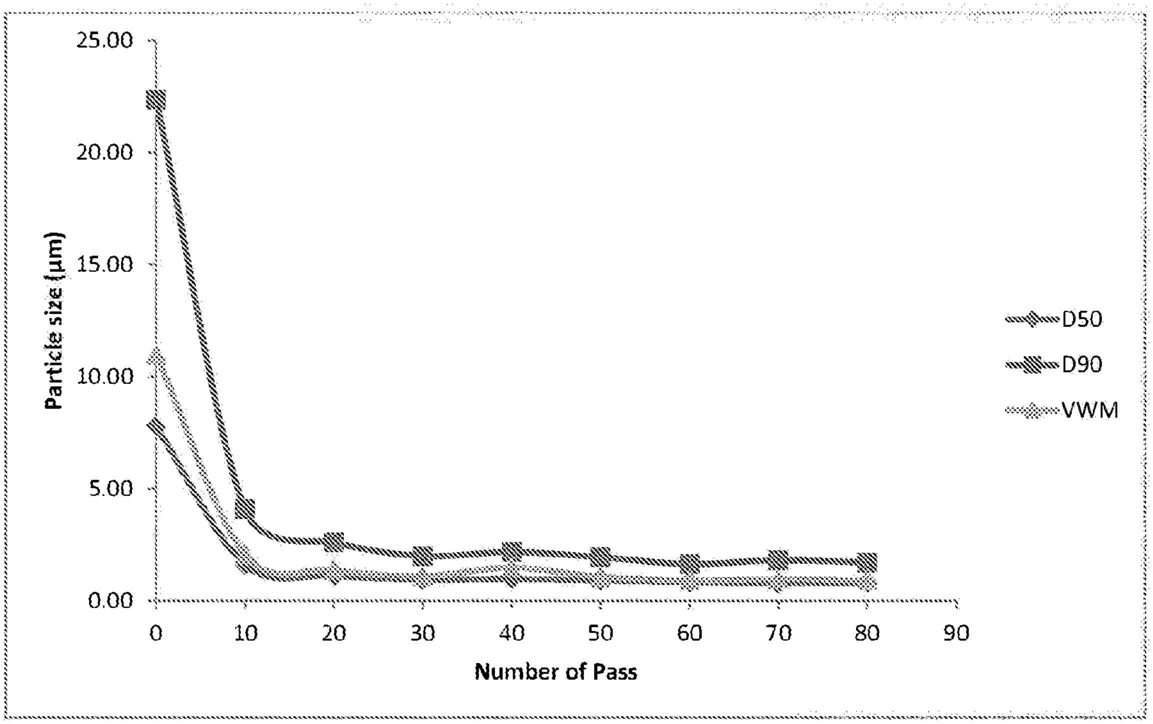
FIG. 2 is a graphical representation of lurasidone particle size distributions in a non-aqueous hydrophobic lipid vehicle suspension, prepared via various number of passes using a wet milling process of ball/media milling.
Figure 3A:
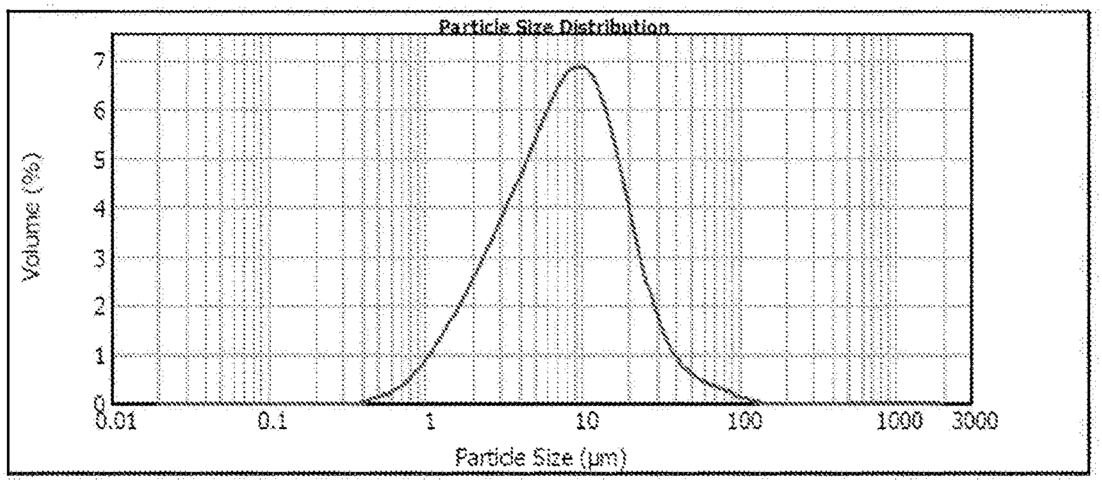
FIG. 3A is a representative lurasidone particle size distribution of a long acting injectable formulation of lurasidone in a non-aqueous hydrophobic lipid vehicle, prepared without a wet milling process of ball/media milling.
Figure 3B:
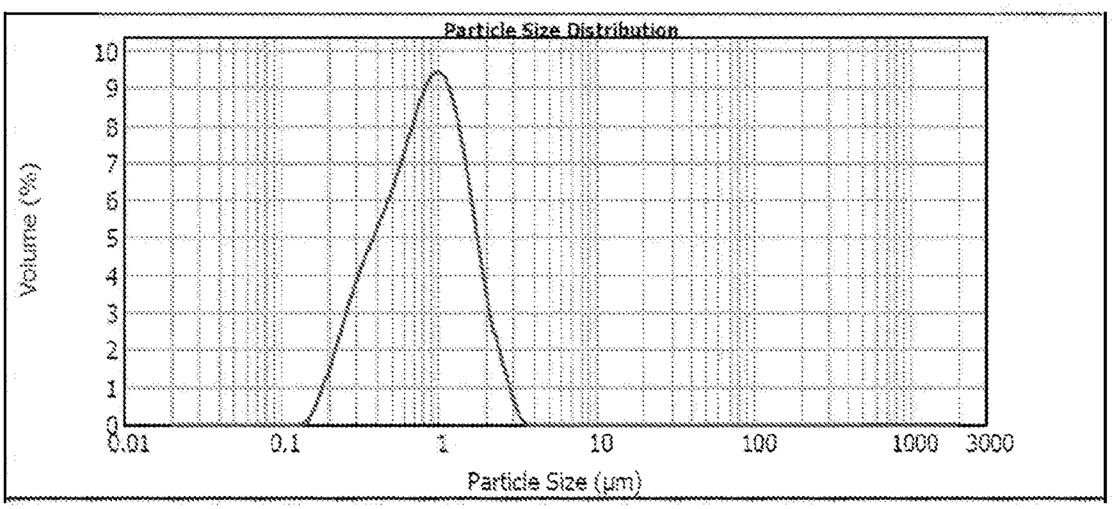
FIG. 3B is a representative lurasidone particle size distribution of a long acting injectable formulation of lurasidone in a non-aqueous hydrophobic lipid vehicle, prepared using a wet milling process of ball/media milling.

Milling was performed for a total of 80 passes. Throughout milling, samples were removed after every 10 passes and evaluated for particle size distribution using a Malvern Mastersizer 2000 Particle Size Distribution Analyzer. The following particle size distribution was determined at the end of 80 passes: $D_{10}$=0.32 μm, $D_{50}$=0.83 μm, $D_{90}$=1.72 μm, VWM=0.94 μm and specific surface area=11.90. A representative lurasidone particle size distribution in a non-aqueous hydrophobic lipid vehicle suspension, prepared via a various number of passes using a wet milling process of ball/media milling is shown in FIG. 2, and the data are listed in Table 4. FIGS. 3A and 3B represent lurasidone particle size distributions of a long acting injectable formulation of lurasidone in a non-aqueous hydrophobic lipid vehicle, prepared without a wet milling process of ball/media milling and using a wet milling process of ball/media milling, respectively.

TABLE 4

| Pass # | $D_{10}$ (μm) | $D_{50}$ (μm) | $D_{90}$ (μm) | VWM (μm) | SSA ($m^2/g$) |
|---|---|---|---|---|---|
| premill | 2.09 | 7.80 | 22.36 | 10.99 | 1.60 |
| 10th | 0.66 | 1.64 | 4.11 | 2.09 | 5.82 |
| 20th | 0.50 | 1.13 | 2.63 | 1.38 | 8.03 |
| 30th | 0.45 | 0.96 | 2.02 | 1.11 | 9.25 |
| 40th | 0.46 | 0.99 | 2.19 | 1.49 | 9.01 |
| 50th | 0.44 | 0.93 | 1.96 | 1.08 | 9.56 |
| 60th | 0.33 | 0.86 | 1.65 | 0.94 | 11.50 |
| 70th | 0.37 | 0.81 | 1.83 | 0.98 | 11.00 |
| 80th | 0.32 | 0.83 | 1.72 | 0.94 | 11.90 |

A long acting injectable formulation of lurasidone in a non-aqueous hydrophobic lipid vehicle prepared using a wet milling process of ball milling exhibited thixotropy. Surprisingly, the inventors of the present invention, found that the hydrophobic lipid vehicle had a viscosity of 0.6 poise, and API suspension in the same hydrophobic lipid vehicle had viscosity of 2.65 poise, at shear rate 10/s, which constituted a 440% increase in viscosity. The viscosity at a shear rate of 100/s decreased to 1.40 poise. See Table 5. This is advantageous because at low or no shear, the high viscosity retards sedimentation, and at the higher shear, it allows flow through a syringe needle. Three (3) mL of the above mentioned suspension were filled into syringes or vials for administration.

TABLE 5

| Lurasidone HCI Suspension in Sesame Oil (milled through ball mill) Viscosity (Poise) at Shear rate (1/s) | | | | | | | |
|---|---|---|---|---|---|---|---|
| Shear Rate (1/s) | 0.25 | 1 | 2.5 | 10 | 25 | 100 | 500 |
| Viscosity (Poise) | 42.41 | 12.06 | 5.802 | 2.652 | 1.899 | 1.396 | 1.138 |

The viscosity and drug release of the suspension was tailored with addition of castor oil. See Table 6.

TABLE 6

| % Castor oil added to Lurasidone Suspension in | Viscosity (Poise) at Shear Rate (1/s) | | | | | | |
|---|---|---|---|---|---|---|---|
| Sesame Oil | 0.25 | 1 | 2.5 | 10 | 25 | 100 | 500 |
| 0 | 42.41 | 12.06 | 5.802 | 2.652 | 1.899 | 1.396 | 1.138 |
| 1 | 119.0 | 32.87 | 15.12 | 5.713 | 3.445 | 1.975 | 1.356 |
| 2 | 132.6 | 39.51 | 18.63 | 7.041 | 4.187 | 2.343 | 1.572 |
| 4 | 124.7 | 37.77 | 17.94 | 6.970 | 4.210 | 2.398 | 1.630 |
| 6 | 146.9 | 43.68 | 20.87 | 7.883 | 4.655 | 2.585 | 1.707 |
| 8 | 140.9 | 43.82 | 21.09 | 8.091 | 4.775 | 2.641 | 1.721 |

Figure 4:
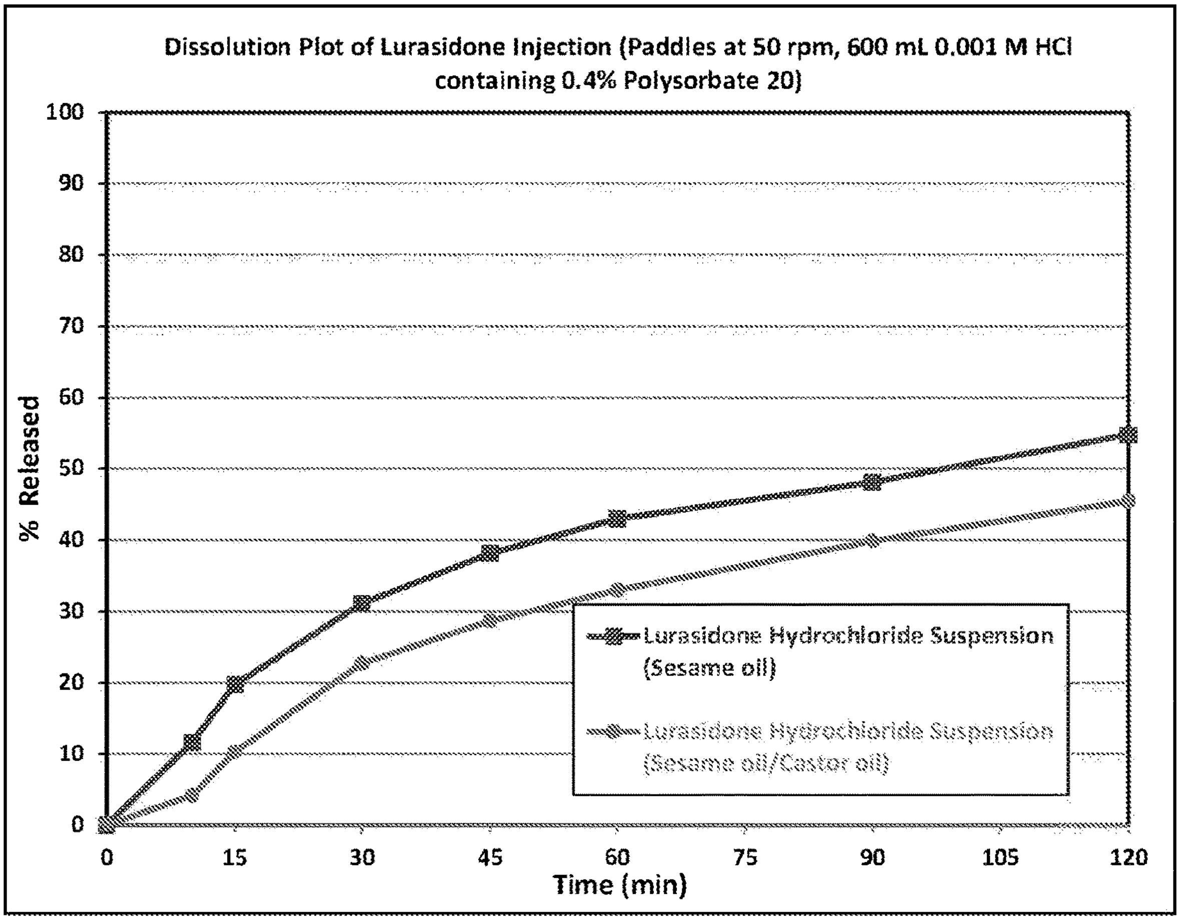
FIG. 4 is a representative in vitro drug release profile of various long acting injectable formulations of lurasidone in non-aqueous hydrophobic lipid vehicles.

The in-vitro drug release from the suspension of Lurasidone hydrochloride was carried out by using USP apparatus 2 (Paddle Apparatus), similar methodology is approved by the FDA to measure the dissolution of Invega Sustenna ° Paliperidone palmitate long acting injectable suspension, a once-a-month product. The drug release was measured over 2 hours in 600 mL of dissolution medium consisting of 0.001M hydrochloric acid containing 0.4% Polysorbate 20 using paddles at 50 rpm with a temperature of 37° C.±0.5° C. Aliquots of release medium were withdrawn at different intervals, and analyzed for the drug content using isocratic, reversed-phase HPLC with ultra-violet wavelength absorption detection at 230 nm. An isocratic elution method was used with mixture of 0.4% trifluoroacetic acid and acetonitrile (60/40, v/v) with a flow rate of 1.0 mL/min and 10 μL of injection volume at 40° C. column temperature. FIG. 4 shows in vitro drug release profiles of various long acting injectable formulations of lurasidone in non-aqueous hydrophobic lipid vehicles.

Surprisingly, the inventors of the present invention found that though the resultant suspension had high viscosity, it could be easily injected to patients as indicated by syringeability data. See Table 7.

TABLE 7

| | Test Speed | Lurasidone Hydrochloride hydrophobic lipid suspension (Sesame oil) | | Lurasidone Hydrochloride hydrophobic lipid suspension (Sesame oil/castor oil ~13.95:1.00) | |
|---|---|---|---|---|---|
| Needle | (mm/sec) | Force (N) | Time (Sec) | Force (N) | Time (Sec) |
| 21G x 1" (0.8 mm x 25 mm) | 0.29 | 4.165 | 80.93 | 5.636 | 77.61 |
| | 0.15 | 2.902 | 150.6 | 3.344 | 172.0 |
| 20G x 2" (0.9 mm x 50 mm) | 0.15 | 3.398 | 170.8 | 4.590 | 168.0 |

*G = Needle Gauge (thickness) and inch (") = Needle Length

The milled hydrophobic lipid suspension is stable with no change in assay and impurity upon storage. In addition no crystal growth of milled particles was observed.

Example—3

A long acting injectable formulation of lurasidone in a non-aqueous hydrophobic lipid vehicle was prepared using a wet milling process of a high pressure homogenizer (Mini DE-BEE, BEE International Group, MA, USA). The following ingredients, as shown in Table 8, were added to a stainless steel vessel to form a dispersion.

TABLE 8

| Ingredient | mg per Dose |
|---|---|
| Lurasidone hydrochloride | 300 |
| Sorbitan monooleate | 30 |
| Sesame oil | q.s. to 3 mL |
| Total | 3 mL |

Figure 5:
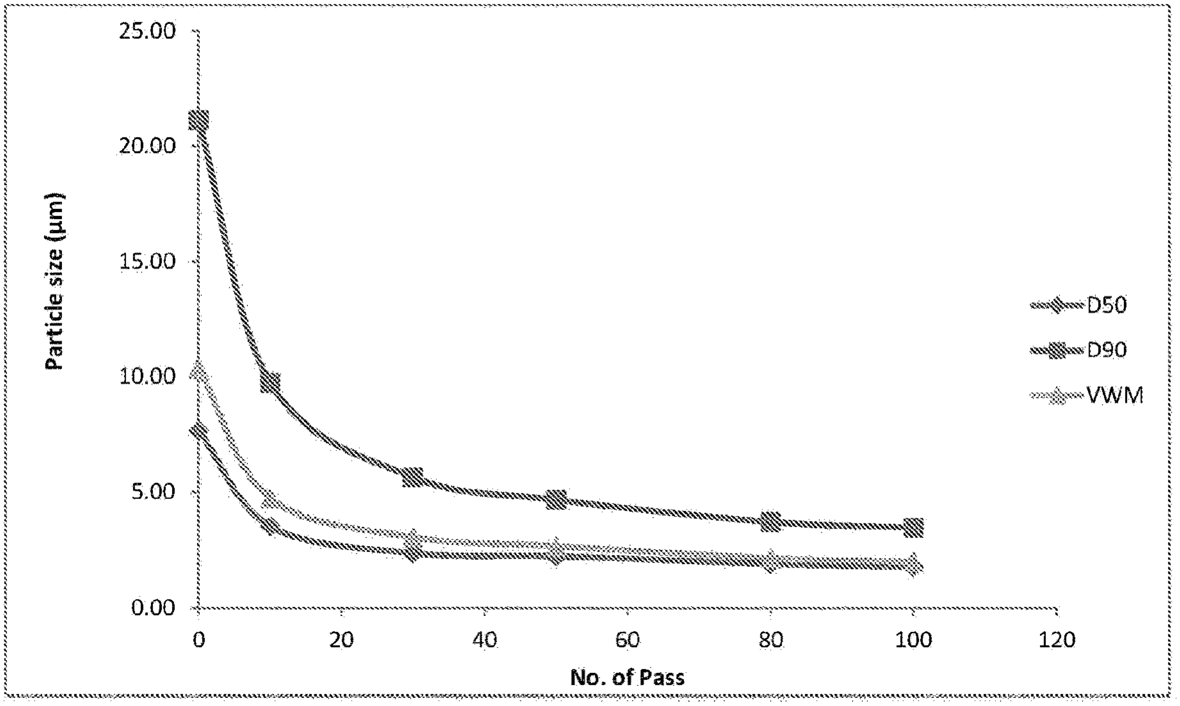
FIG. 5 is a graphical representation of lurasidone particle size distribution in a non-aqueous hydrophobic lipid vehicle suspension, prepared via various number of passes using a wet milling process of high pressure homogenizer milling.
Figure 6A:
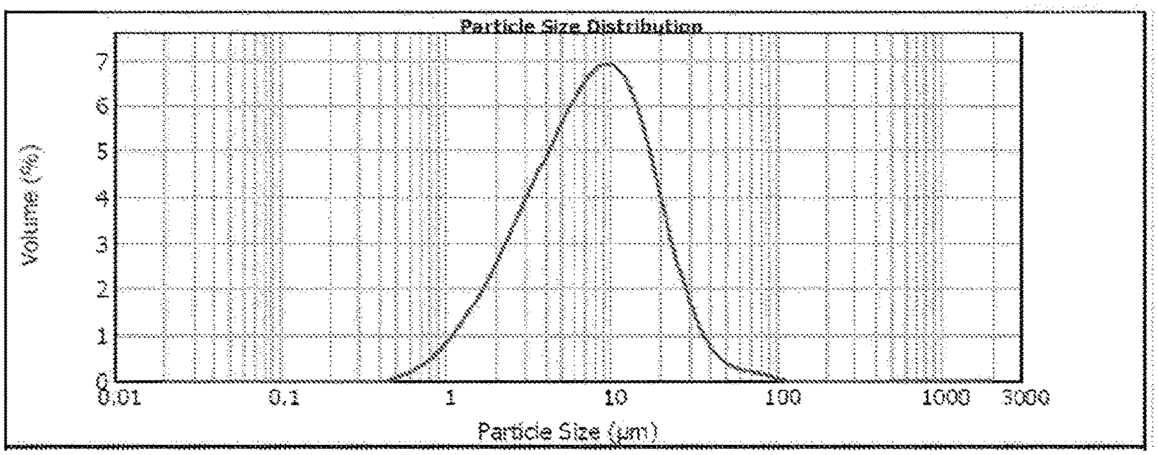
FIG. 6A is a representative lurasidone particle size distribution of a long acting injectable formulation of lurasidone in a non-aqueous hydrophobic lipid vehicle, prepared without a wet milling process of high pressure homogenizer milling.
Figure 6B:
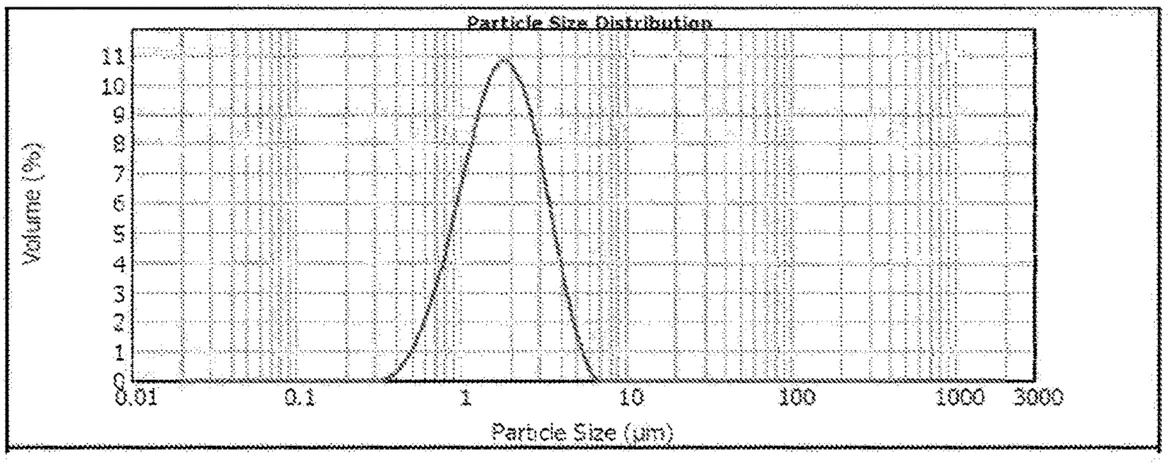
FIG. 6B is a representative lurasidone particle size distribution of a long acting injectable formulation of lurasidone in a non-aqueous hydrophobic lipid vehicle, prepared using a wet milling process of high pressure homogenizer milling.

The particle size reduction was performed using a high pressure homogenizer at 25,000 psi. At various pass intervals, a sample was removed and evaluated for particle size distribution using a Malvern Mastersizer 2000 Particle Size Distribution Analyzer. After the 100th pass, the following particle size distribution was determined: $D_{10}$=0.84 μm, $D_{50}$=1.77 μm, $D_{90}$=3.46 μm. A graphical representation of lurasidone particle size distribution in a non-aqueous hydrophobic lipid vehicle suspension, prepared via a various number of passes using a wet milling process of high pressure homogenizer milling is shown in FIG. 5, and the data are listed in Table 9. FIGS. 6A and 6B represent a lurasidone particle size distribution of a long acting injectable formulation of lurasidone in a non-aqueous hydrophobic lipid vehicle, prepared without a wet milling process of high pressure homogenizer milling and using a wet milling process of high pressure homogenizer milling respectively.

TABLE 9

| Pass # | $D_{10}$ (μm) | $D_{50}$ (μm) | $D_{90}$ (μm) | VWM (μm) | SSA ($m^2/g$) |
|---|---|---|---|---|---|
| Premill | 2.15 | 7.64 | 21.13 | 10.33 | 1.58 |
| 10th | 1.36 | 3.52 | 9.73 | 4.73 | 2.78 |
| 30th | 1.03 | 2.36 | 5.65 | 3.05 | 3.89 |
| 50th | 1.04 | 2.23 | 4.66 | 2.66 | 4.04 |
| 80th | 0.91 | 1.90 | 3.71 | 2.14 | 4.70 |
| 100th | 0.84 | 1.77 | 3.46 | 1.99 | 5.06 |

A long acting injectable formulation of lurasidone in a non-aqueous hydrophobic lipid vehicle prepared using a wet milling process of a high shear homogenizer also exhibited thixotropy. The suspension had a viscosity of 6.38 poise at 1/s shear rate, 1.81 poise at 10/s shear rate, and a viscosity of 1.10 at a 100/s shear rate. See Table 10. Three (3) mL of the above mentioned suspension were filled into syringes or vials for administration.

TABLE 10

| Lurasidone HCI Suspension in Sesame Oil (milled in a High Pressure Homogenizer) Viscosity (Poise) at Shear Rate (1/s) | | | | | | | |
|---|---|---|---|---|---|---|---|
| Shear Rate (1/s) | 0.25 | 1 | 2.5 | 10 | 25 | 100 | 500 |
| Viscosity (Poise) | 22.07 | 6.377 | 3.369 | 1.808 | 1.400 | 1.096 | 0.9226 |

The milled hydrophobic lipid suspension was stable with no change in assay and impurity. No crystal growth of milled particles was observed.

Example—4

A long acting injectable formulation of lurasidone in a hydrophilic organic compound was prepared using a wet milling process of ball/media milling.

The formulation for a long acting injection of lurasidone HCl in a hydrophilic vehicle is listed in Table 11 below:

TABLE 11

| Ingredient | mg per Dose |
|---|---|
| Lurasidone hydrochloride | 300.0 |
| Polysorbate 20 | 30.00 |
| Polyethylene Glycol 400 | q.s. to 3 mL |
| Total | 3 mL |

Figure 7:
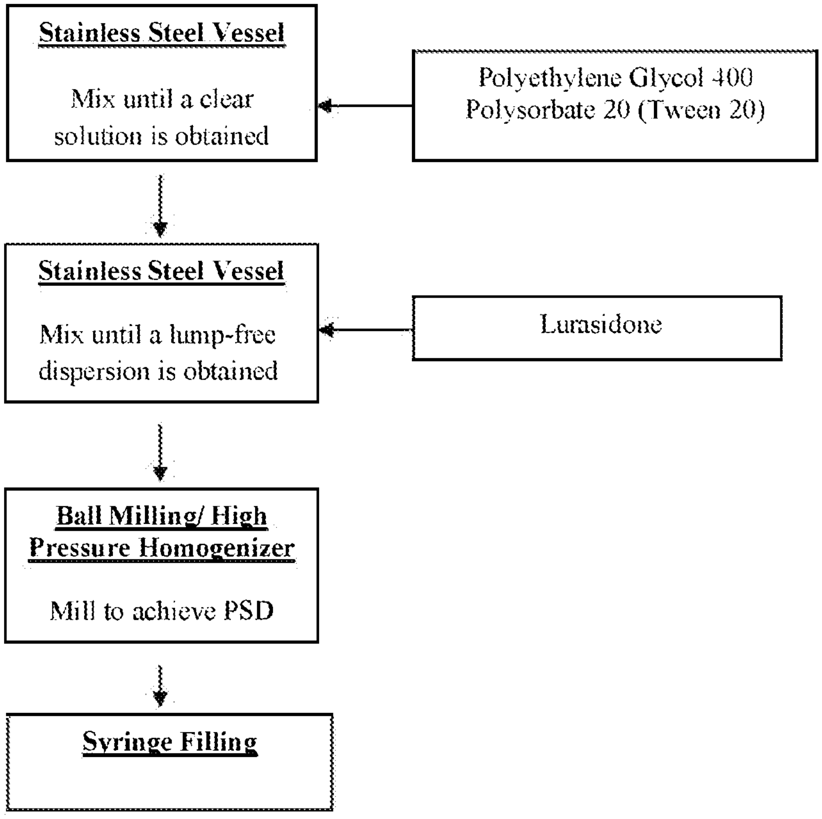
FIG. 7 depicts a representative flow chart for making a long acting injectable formulation of lurasidone in a non-aqueous hydrophilic organic compound, using a wet milling process of ball/media or high pressure homogenizer milling.

As shown in FIG. 7, lurasidone HCl was mixed with polyethylene glycol 400 and an amphiphilic agent, polysorbate 20. The dispersed lurasidone was further milled using a wet milling process of ball milling.

At various pass intervals, a sample was removed and evaluated for particle size distribution using a Malvern Mastersizer 2000 Particle Size Distribution Analyzer. After the 50th pass, the following particle size distribution was determined: $D_{10}$=0.13 μm, $D_{50}$=0.29 μm, $D_{90}$=0.70 μm. The decrease in particle size with number of passes is described in Table 12 below.

TABLE 12

| Pass # | $D_{10}$ (μm) | $D_{50}$ (μm) | $D_{90}$ (μm) | VWM (μm) | SSA ($m^2/g$) |
|---|---|---|---|---|---|
| Premill | 4.12 | 12.43 | 34.04 | 16.51 | 1.00 |
| 10th | 0.16 | 0.37 | 1.27 | 0.66 | 24.00 |
| 20th | 0.15 | 0.33 | 0.81 | 0.46 | 27.50 |
| 30th | 0.13 | 0.30 | 0.71 | 0.37 | 31.70 |
| 40th | 0.13 | 0.30 | 0.73 | 0.38 | 30.70 |
| 50th | 0.13 | 0.29 | 0.70 | 0.36 | 32.10 |

A long acting injectable formulation of lurasidone in a hydrophilic organic compound was thixotropic. The suspension had a viscosity of 6.94 poise at a shear rate of 1/s, 3.35 poise at a shear rate of 10/s, and 2.04 poise at a shear rate of 100/s. See Table 13. Three (3) mL of above mentioned suspension were filled into syringes or vials for administration.

TABLE 13

| Lurasidone HCI Suspension in PEG400 (Milled through Ball Mill) Viscosity (Poise) at Shear Rate (1/s) | | | | | | | |
|---|---|---|---|---|---|---|---|
| Shear Rate (1/s) | 0.25 | 1 | 2.5 | 10 | 25 | 100 | 500 |
| PEG400 suspension | 12.42 | 6.939 | 5.098 | 3.355 | 2.668 | 2.041 | 1.662 |

Example—5

A long acting injectable formulation of lurasidone in a non-aqueous hydrophobic lipid vehicle or a hydrophilic organic compound was prepared using a dry milling process of an air jet mill.

TABLE 14

| Ingredient | mg per Dose |
|---|---|
| Lurasidone HCl (Air jet milled) | 300.0 |
| Sorbitan monooleate | 30.00 |
| Sesame oil | q.s. to 3 mL |
| Total | 3 mL |

Figure 8:
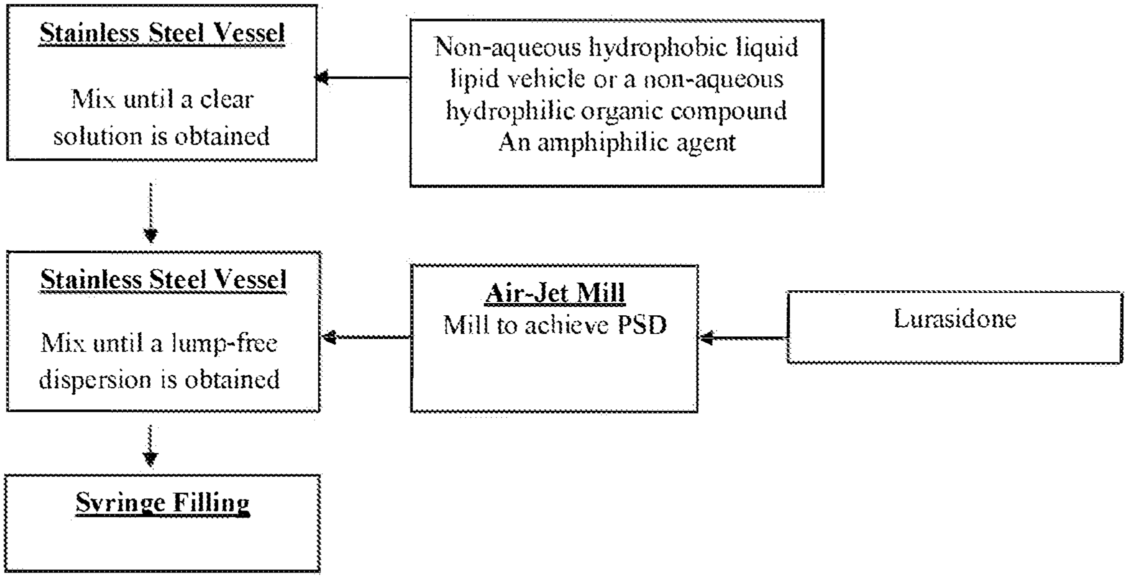
FIG. 8 depicts a representative flow chart for making a long acting injectable formulation of lurasidone in a non-aqueous hydrophobic lipid vehicle or a non-aqueous hydrophilic organic compound, using a dry milling process of air jet mill.

As shown in FIG. 8, a desired particle size distribution of lurasidone API, such as a $D_{90}$ particle size of about 25 μm or less, can be achieved via a dry milling process of an air jet mill. Then the milled API can be dispersed in a non-aqueous hydrophobic lipid vehicle or a hydrophilic organic compound containing an amphiphilic agent. The resulting suspension can be filled into a syringe or vial for administration.

Example—6

A long acting injectable formulation of ziprasidone in a non-aqueous hydrophobic lipid vehicle was prepared using a wet milling process of ball/media or high pressure homogenizer milling.

Figure 9:
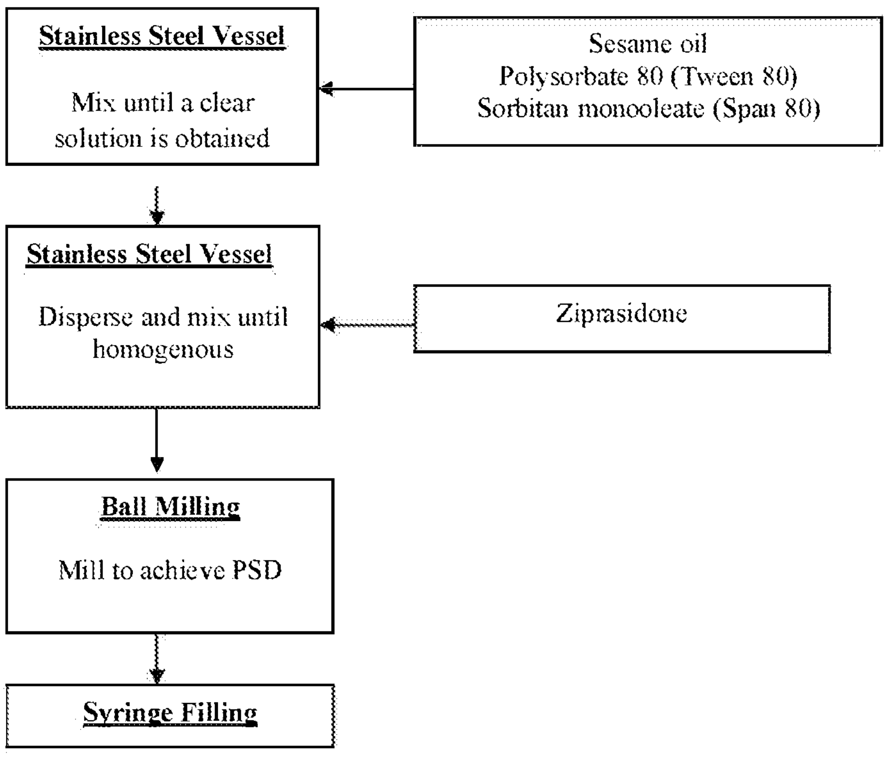
FIG. 9 depicts a representative flow chart for making a long acting injectable formulation of ziprasidone in a non-aqueous hydrophobic lipid vehicle, using a wet milling process of ball/media or high pressure homogenizer milling.

A suspension of ziprasidone was prepared using a wet milling process of a DYNO®-MILL (Type KDL Special, manufactured by Basel, Switzerland) as described in FIG. 9.

The following ingredients, as shown in Table 15, were added to a stainless steel vessel to form dispersion.

TABLE 15

| Ingredient | mg per Dose |
|---|---|
| Ziprasidone hydrochloride | 300.0 |
| Polysorbate 80 | 30.00 |
| Sorbitan monooleate | 186.0 |
| Sesame oil | q.s. to 2.5 mL |
| Total | 2.5 mL |

The grinding chamber was filled to 80% capacity with yttrium-stabilized zirconium oxide beads, and the suspension was passed through the mill operated at the conditions shown in Table 16.

TABLE 16

| Grinding chamber | Water-cooled jacketed 0.3 L |
|---|---|
| Motor tip speed | 10 meters/sec |
| Grinding medium | 240 mL of yttrium stabilized zirconium oxide beads |
| Suspension flow rate | 140 g/min |

Figure 10:
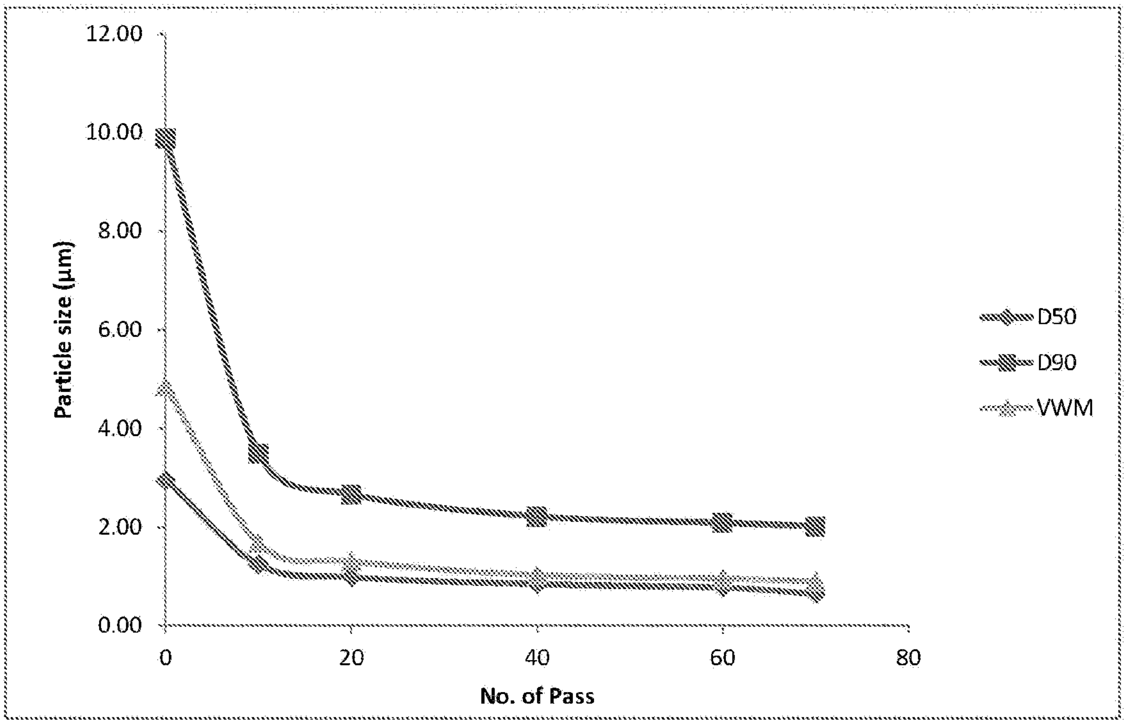
FIG. 10 is a graphical representation of ziprasidone particle size distribution in a non-aqueous hydrophobic lipid vehicle suspension, prepared via various number of passes using a wet milling process of ball/media milling.

At various pass intervals, a sample was removed and evaluated for particle size distribution using a Malvern Mastersizer 2000 Particle Size Distribution Analyzer. The following particle size distribution was determined after the $70^{th}$ pass: $D_{10}$=0.16 μm, $D_{50}$=0.65 μm, $D_{90}$=2.02 μm, VWM=0.90 μm and specific surface area=11.20. A graphical representation of ziprasidone particle size distribution in a non-aqueous hydrophobic lipid vehicle suspension, prepared via various number of passes using a wet milling process of ball/media milling is shown in FIG. 10, and the data are listed Table 17 below:

TABLE 17

| Pass # | D10 (μm) | D50 (μm) | D90 (μm) | VWM (μm) | SSA ($m^2$/g) |
|---|---|---|---|---|---|
| premill | 1.16 | 2.94 | 9.89 | 4.87 | 1.85 |
| 10th | 0.23 | 1.24 | 3.49 | 1.69 | 7.17 |
| 20th | 0.20 | 0.98 | 2.66 | 1.30 | 8.44 |
| 40th | 0.17 | 0.84 | 2.22 | 1.03 | 9.97 |
| 60th | 0.17 | 0.77 | 2.09 | 0.96 | 10.50 |
| 70th | 0.16 | 0.65 | 2.02 | 0.90 | 11.20 |

A long acting injectable formulation of ziprasidone HCl in a hydrophobic lipid vehicle was prepared using a wet milling process of ball milling. The resultant suspension was thixotropic, and the suspension had a viscosity of 9.42 poise at 1/s shear rate, 3.28 poise at 10/s shear rate, and 1.95 poise at a 100/s shear rate. See Table 18.

TABLE 18

| Ziprasidone HCI Suspension in Sesame Oil (Milled through Ball-Mill) Viscosity (Poise) at Shear Rate (1/s) | | | | | | | |
|---|---|---|---|---|---|---|---|
| Shear Rate (1/s) | 0.25 | 1 | 2.5 | 10 | 25 | 100 | 500 |

TABLE 18-continued

| | Ziprasidone HCI Suspension in Sesame Oil (Milled through Ball-Mill) Viscosity (Poise) at Shear Rate (1/s) | | | | | | |
|---|---|---|---|---|---|---|---|
| Viscosity (Poise) | 23.83 | 9.422 | 5.918 | 3.281 | 2.500 | 1.952 | 1.766 |

Example—7

Several long acting injectable formulations (Tables 19-21) of meloxicam in hydrophobic lipid vehicles were prepared by adding meloxicam to the mixed vehicles and dispersing the drug using a vortexer. The viscosity of the formulations at 10/s shear rate are listed in the table. The particle size of meloxicam, determined by sieve analysis, is that 92.9% of the particles, by weight, were less than 10 microns.

TABLE 19

| Ingredients | 100 mg/mL | | | | | | | | | | | |
|---|---|---|---|---|---|---|---|---|---|---|---|---|
| Meloxicam | 100 | 100 | 100 | 100 | 100 | 100 | 100 | 100 | 100 | 100 | 100 | 100 |
| Sorbitan Monooleate | — | 10 | — | — | — | 10 | — | 10 | — | 10 | — | 10 |
| Polyethylene Glycol 400 | — | — | — | — | — | — | 10 | 10 | — | 10 | — | — |
| Benzyl Alcohol | — | — | — | — | — | — | — | — | 10 | — | — | — |
| Castor oil | — | — | 10 | 50 | 450 | 445 | — | — | — | — | Q.s to 1 mL | Q.s to 1 mL |
| Sesame oil | Q.s to 1 mL | Q.s to 1 mL | Q.s to 1 mL | Q.s to 1 mL | Q.s to 1 mL | Q.s to 1 mL | Q.s to 1 mL | Q.s to 1 mL | Q.s to 1 mL | Q.s to 1 mL | — | — |
| Total | 1 | 1 | 1 | 1 | 1 | 1 | 1 | 1 | 1 | 1 | 1 | 1 |
| Viscosity (poise)* | 0.915 | 1.347 | 0.9306 | 1.004 | 2.610 | 2.615 | 1.015 | 2.905 | 0.833 | 2.215 | 10.86 | 10.43 |

*Viscosity is reported at 10/s shear rate

TABLE 20

| Ingredients | 200 mg/mL | | | | | | | | | |
|---|---|---|---|---|---|---|---|---|---|---|
| Meloxicam | 200 | 200 | 200 | 200 | 200 | 200 | 200 | 200 | 200 | 200 | 200 |
| Sorbitan Monooleate | — | 10 | — | — | 10 | — | 10 | — | 10 | — | 10 |
| Polyethylene Glycol 400 | — | — | — | — | — | 10 | 10 | — | 10 | — | — |
| Benzyl Alcohol | — | — | — | — | — | — | — | 10 | — | — | — |
| Castor oil | — | — | 50 | 450 | 445 | — | — | — | — | Q.s to 1 mL | Q.s to 1 mL |
| Sesame oil | Q.s to 1 mL | Q.s to 1 mL | Q.s to 1 mL | Q.s to 1 mL | Q.s to 1 mL | Q.s to 1 mL | Q.s to 1 mL | Q.s to 1 mL | Q.s to 1 mL | — | — |
| Total | 1 | 1 | 1 | 1 | 1 | 1 | 1 | 1 | 1 | 1 | 1 |
| Viscosity (Poise) | 1.574 | 2.430 | 2.121 | 4.765 | 4.875 | 2.590 | 8.601 | 1.438 | 2.238 | 14.99 | 15.77 |

*Viscosity at 10/s shear rate

TABLE 21

| Ingredients | 300 mg/mL | | | | | |
|---|---|---|---|---|---|---|
| Meloxicam | 300 | 300 | 300 | 300 | 300 | 300 |
| Sorbitan Monooleate | — | 10 | — | 10 | — | 10 |
| Polyethylene Glycol 400 | — | — | — | — | — | — |
| Benzyl Alcohol | — | — | — | — | — | — |
| Castor oil | — | — | 450 | 445 | Q.s to 1 mL | Q.s to 1 mL |
| Sesame oil | Q.s to 1 mL | Q.s to 1 mL | Q.s to 1 mL | Q.s to 1 mL | — | — |
| Total | 1 | 1 | 1 | 1 | 1 | 1 |
| Viscosity (Poise)* | 4.457 | 7.650 | 9.523 | 11.02 | 27.55 | 27.99 |

*Viscosity at 10/s shear rate

Example—8

Several long acting injectable formulations (Table 22) of adefovir dipivoxil in hydrophobic lipid vehicles were prepared by adding adefovir dipivoxil to the mixed vehicles and dispersing the drug using a vortexer. The viscosity of the formulations at 10/s shear rate are listed in the table.

TABLE 22

| Ingredients | 100 mg/mL | | | | | | | | | | |
|---|---|---|---|---|---|---|---|---|---|---|---|
| Adefovir Dipivoxil | 100 | 100 | 100 | 100 | 100 | 100 | 100 | 100 | 100 | 100 | 100 |
| Sorbitan Monooleate | — | 10 | 50 | — | 10 | — | — | — | — | 10 | 10 |
| Polyethylene Glycol 400 | — | — | — | — | — | 10 | — | — | — | — | — |
| Benzyl Alcohol | — | — | — | — | — | — | 10 | — | — | — | — |
| Castor oil | — | — | — | 450 | 455 | — | — | Q.s to 1 mL | — | — | — |
| Cottonseed oil | — | — | — | — | — | — | — | — | Q.s to 1 mL | Q.s to 1 mL | 455 |
| Sesame oil | Q.s to 1 mL | Q.s to 1 mL | Q.s to 1 mL | Q.s to 1 mL | Q.s to 1 mL | Q.s to 1 mL | Q.s to 1 mL | — | — | — | Q.s to 1 mL |
| Total | 1 | 1 | 1 | 1 | 1 | 1 | 1 | 1 | 1 | 1 | 1 |
| Viscosity (Poise)* | 1.194 | 1.938 | 1.907 | 2.855 | 3.065 | 3.342 | 1.885 | 11.89 | 0.9091 | 1.894 | 3.397 |

*Viscosity at 10/s shear rate.

Example—9

Figure 11:
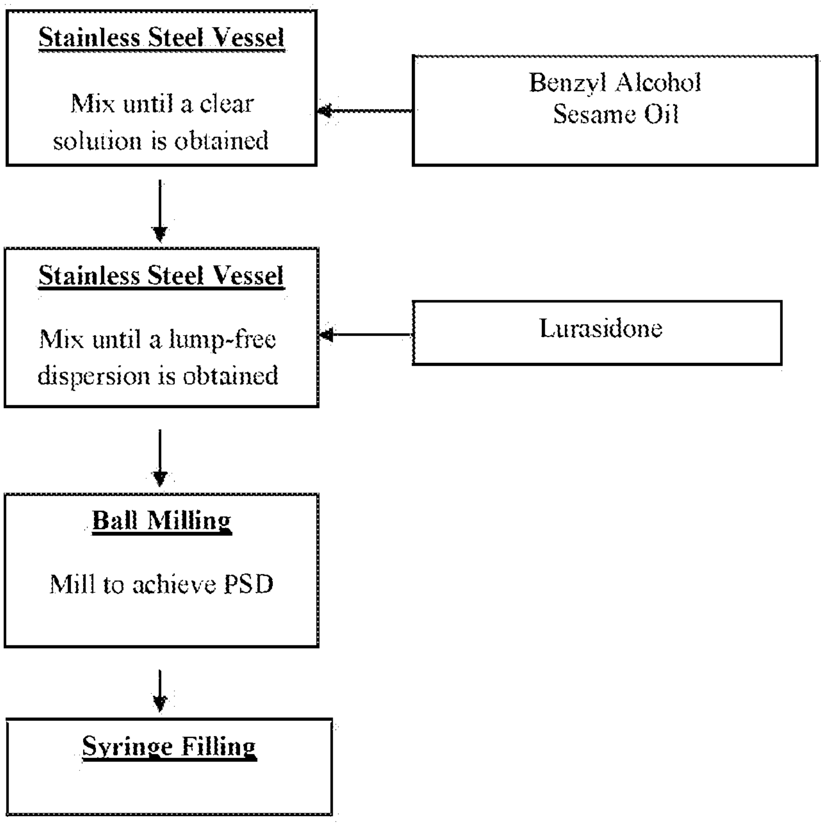
FIG. 11 depicts a representative flow chart of making a long acting injectable formulation of lurasidone in a non-aqueous hydrophobic lipid vehicle of sesame oil and benzyl alcohol, prepared using a wet milling process of ball/media milling.
Figure 12:
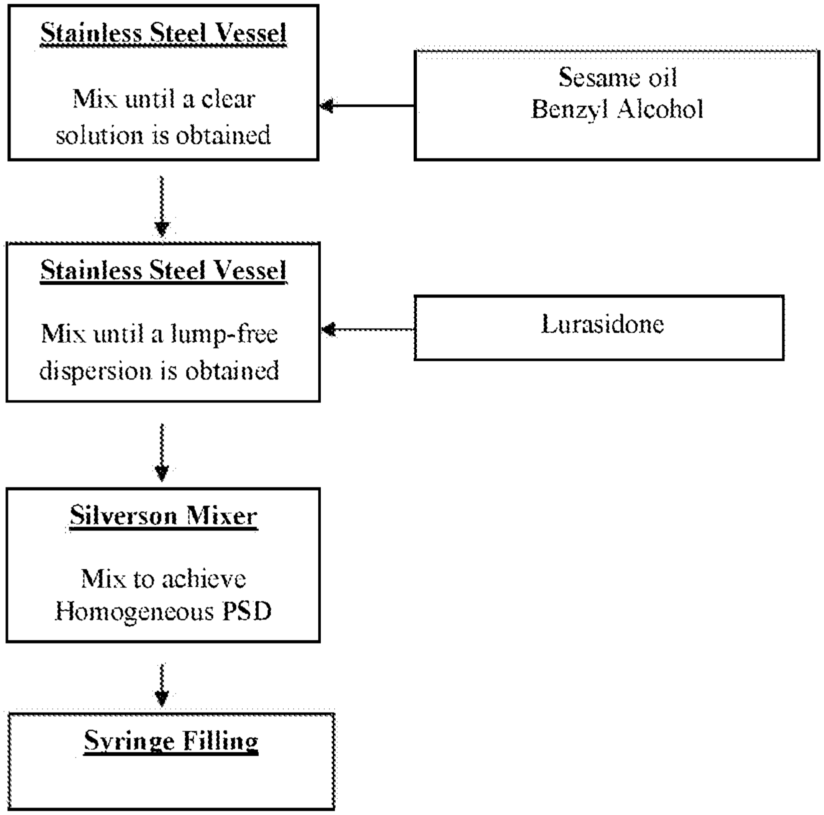
FIG. 12 depicts a representative flow chart of making a long acting injectable formulation of lurasidone in a non-aqueous hydrophobic lipid vehicle of sesame oil and benzyl alcohol, prepared using dispersion and mixing.
Figure 13:
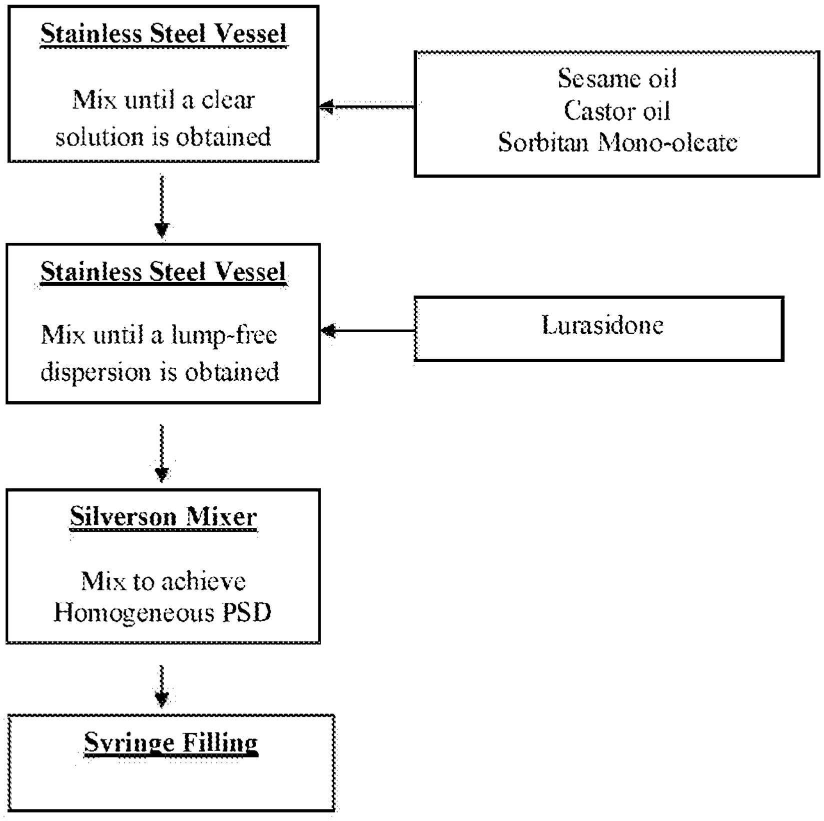
FIG. 13 depicts a representative flow chart of making a long acting injectable formulation of lurasidone in a non-aqueous hydrophobic lipid vehicle of sesame oil, castor oil and sorbitan monooleate, prepared using dispersion and mixing.
Figure 14:
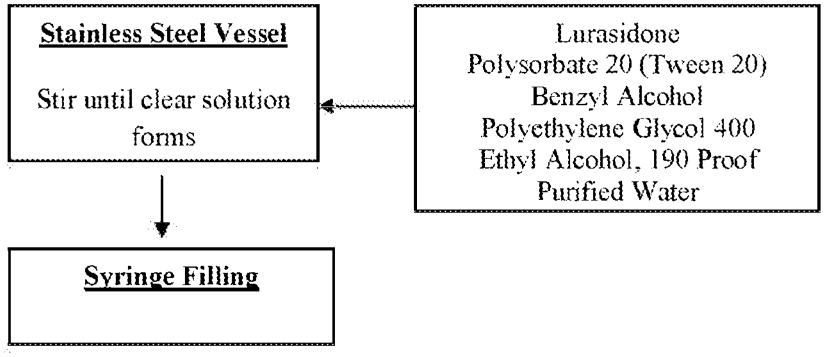
FIG. 14 depicts a representative flow chart of making a lurasidone solution in an aqueous-base vehicle.

A long acting formulation is expected to suppress the maximum blood concentration ($C_{max}$) and maintain therapeutic blood profiles for an extended period of time. Hence, the desired pharmacokinetic performance of a long acting formulation is a lower Cmax, a higher AUC/$C_{max}$ ratio, a longer half-life ($t_{1/2}$) and a longer Mean Residence Time (MRT, (T½/ln2)) compared to an immediate release product. To evaluate the in-vivo performance of our formulations, three suspensions of Lurasidone HCl were prepared with varying particle size and/or viscosity at 100 mg/mL with compositions given in Table 23, and with processes shown in FIGS. 11, 12 and 13 for Suspensions 1, 2, and 3, respectively. As a control, a solution of Lurasidone HCl was prepared at 2.5 mg/mL. Its composition is given in Table 24, and with the process shown in FIG. 14. A four arm parallel study (n=5 rats per arm) in male Sprague-Dawley Rats under fasted conditions was conducted to determine the pharmacokinetic profiles of the long acting injectable formulations described in this patent. The four formulations were administered by intramuscular injection, under fasted conditions, and blood was sampled at specified time intervals through 720 hours through a Jugular vein cannulae, ~0.3 mL.

TABLE 23

Compositions of Lurasidone Suspensions for Pharmacokinetic Study

| Ingredient | mg/mL | | |
|---|---|---|---|
| | Suspension 1 | Suspension 2 | Suspension 3 |
| Lurasidone Hydrochloride | 100 | 100 | 100 |
| Sorbitan Monooleate, (Span 80) | — | — | 10 |
| Benzyl Alcohol | 5 | 5 | — |
| Super Refined Castor Oil | — | — | 445 |
| Super Refined Sesame Oil | Q.s to 1 mL | Q.s to 1 mL | Q.s to 1 mL |
| Total (mL) | 1 | 1 | 1 |

TABLE 24

Compositions of Lurasidone Solution for Pharmacokinetic Study

| Ingredient | Concentration (mg/mL) |
|---|---|
| Lurasidone Hydrochloride | 2.500 |
| Polysorbate 20 (Tween 20) | 10.00 |
| Benzyl Alcohol | 10.00 |
| Polyethylene Glycol 400 | 300.7 |
| Ethyl Alcohol | 200.5 |
| Purified Water | Q.s to 1 mL |
| Total (mL) | 1 |

The blood samples were collected, placed into chilled tubes containing sodium heparin, inverted several times to mix, and kept on ice until centrifugation. The samples were centrifuged at a temperature of 2 to 8° C., at 3,000×g, for 5 minutes. Plasma samples were collected into polypropylene tubes after centrifugation of the blood samples, and stored frozen (−60° C. to −80° C.) until transferred frozen on dry ice for analysis. Samples were analyzed with LC-MS/MS against an eight point standard curve with concentrations ranging from 0.05 ng/mL to 100 ng/mL. Standards were prepared by adding 10 μL of an appropriate working solution to 50 μL of blank matrix. Samples were prepared by adding 10 μL 50:50 acetonitrile:water to 50 μL of study sample. Blanks were prepared by adding 10 μL 50:50 acetonitrile: water to 50 μL of blank matrix A deuterated internal standard (150 μL of Lurasidone-d8) was added to the standard and sample preparations. All solutions were prepared on a 96 well plate. Prior to analysis, the plate was centrifuged at 3000 RPM for five minutes, and the solutions were transferred and injected.

The chromatographic and mass spectrometer conditions are listed below.

HPLC Conditions

Instrument: Waters Acquity UPLC

Column: Waters BEH Phenyl 2.1×30 mm, 1.7 um

Aqueous Reservoir (A): 0.1% formic acid in $H_2O$

Organic Reservoir (B): 0.1% formic acid in MeCN

Gradient Program:

TABLE 25

| Time (min) | Grad. Curve | % A | % B |
|---|---|---|---|
| 0.00 | 6 | 90 | 10 |
| 0.75 | 6 | 0 | 100 |
| 0.80 | 6 | 90 | 10 |
| 1.00 | 6 | 90 | 10 |

Flow Rate: 800 μL/min

Injection Volume: 10 μL

Run Time: 1.0 min

Column Temperature: 40° C.

Sample Temperature: 8° C.

Strong Autosampler Wash: 1:1:1, water:acetonitrile:isopropyl alcohol with 0.2% formic acid Weak Autosampler Wash: 4 mM ammonium formate Mass Spectrometer Conditions Instrument: PE Sciex API4000

Interface: Electrospray ("Turbo Ion Spray")

Mode: Multiple reactions monitoring (MRM)

Gases: CUR 20, CAD 10, GS1 50, GS2 50

Source Temperature: 500° C.

Voltages and Ions Monitored:

TABLE 26

| Analyte | Polarity | Precursor Ion | Product Ion | IS | DP | EP | CE | CXP |
|---|---|---|---|---|---|---|---|---|
| Lurasidone | Positive | 493.4 | 166.2 | 5500 | 120 | 10 | 55 | 11 |
| Lurasidone-d8 (IS) | Positive | 501.4 | 166.2 | 5500 | 120 | 10 | 55 | 11 |

Figure 15:
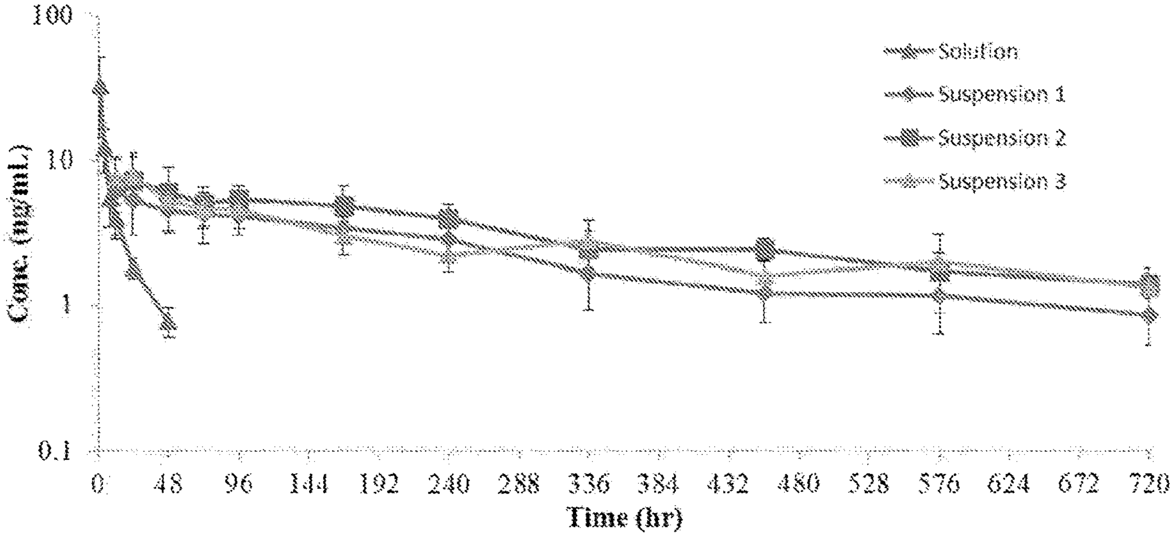
FIG. 15 is a graphical representation of lurasidone plasma concentration versus time profiles for a lurasidone aqueous-based solution and three lurasidone long acting injections that were administered intramuscularly into male Sprague Dawley Rats.

The formulations were well tolerated, and no adverse local or systemic reactions were observed following intramuscular administration of lurasidone to the animals. Key physico-chemical parameters of the formulations and pharmacokinetic parameters from the study are listed in Table 27. (Pharmacokinetic parameters were calculated with Phoenix WinNonlin version 6.4). The plasma concentration versus time curves for the various formulations are shown in FIG. 15. The half-lives of Lurasidone for all suspensions, administered intramuscularly are above 48 hours and are 25 to 50-fold greater than the half-life of the solution administered intramuscularly. The half-lives of the suspensions are much greater than the 18 hour half-life reported for Lurasidone after oral administration of a 40 mg tablet. (Lutuda® package insert, Sunovion Pharmaceuticals, July 2013). The $C_{max}$ for the suspensions are 1% of the dose-adjusted $C_{max}$ of the solution formulation, demonstrating an effective control of drug release from the suspension products. Furthermore, as shown in Table 23, the higher values for t½, $AUC/C_{max}$, and MRT values of the suspension products compared to the solution product, indicate that a long acting pharmacokinetic profile is achieved.

TABLE 27

| Parameters | Lurasidone Hydrochloride Formulations: Suspension 1 | Suspension 2 | Suspension 3 | Solution |
|---|---|---|---|---|
| PSD (D90 μm) | 2.64 | 17.13 | 16.94 | N/A |
| Viscosity (Poise)** | 3.80 | 1.185 | 3.007 | 0.068 |
| Dose (mg/kg) | 45 | 45 | 45 | 1.5 |
| $T_{max}$ (hr) | 30.0 | 43.2 | 19.2 | 1.00 |
| $C_{max}$ (ng/mL) | 5.88 | 7.62 | 8.54 | 33.0 (990.0[1]) |
| $AUC_t$ (hr · ng/mL) | 1611 | 2306 | 1954 | 284 |
| $AUC_\infty$ (hr · ng/mL) | 1939 | 3109 | 2916* | 287 |
| $t_{1/2}$ (hr) | 337 | 252 | 505 | 10*** |
| $AUC_\infty$ / $C_{max}$ (hr) | 330 | 408 | 341 | 8.70 |
| MRT ($t_{1/2}$ / ln2) (hr) | 487 | 347 | 730 | 14.4 |

*Calculated based on $C_{last}$ Viscosity determined at 10/s shear rate. *Calculated based on terminal phase plasma concentrations above 2% of $C_{max}$ [1]Theoretical dose adjusted $C_{max}$, MRT is Mean Residence Time.

The half-life of a drug is an intrinsic, natural property of a drug that is influenced by its distribution, metabolism, elimination and various factors. In the present disclosure, Applicants have demonstrated that by using the novel formulation approach described herein, the half-life of a drug in the present formulation can be greatly increased relative to drug in its simplest form, for example a drug in solution. Table 27 illustrates that this invention, a novel formulation, extends the half-life of lurasidone from 10 hours to as long as 505 hours. The invention, through extension of the half-life, allows the dosing frequency to be reduced from once a day to as long as once a week, once a month, to once every three months.

What is claimed is:

1. A process for preparing a non-aqueous long acting injectable formulation, comprising:

i. mixing about 0.5% to about 10% by weight of the formulation of an amphiphilic agent selected from the group consisting of ethanol, benzyl alcohol, benzyl benzoate, N-methyl-2-pyrrolidone, dimethylacetamide, sorbitan esters, polyethoxylated sorbitan esters, fatty alcohol ethoxylates, fatty acid ethoxylates, polyoxyethylene polyoxypropylene block copolymers, and combinations thereof with about 80% to about 95% by weight of the formulation of a non-aqueous liquid vehicle comprising a hydrophobic lipid comprising a glyceryl ester of a $C_6$-$C_{24}$ fatty acid;

ii. dispersing about 5% to about 20% by weight of the formulation of lurasidone as free base or salt in the mixture of (i) and mixing to form a dispersion, wherein the lurasidone is dispersed as discrete particles; and iii. milling the dispersion of (ii) to achieve lurasidone particles having a $D_{90}$ particle size of about 0.5 μm to about 25 μm to obtain the long acting injectable formulation, wherein the long acting injectable formulation is non-gelling and thixotropic with a viscosity of less than 10 poise at a shear rate of 10/s at 25° C. and a viscosity of greater than 15 poise at a shear rate of less than or equal to about 0.1/s at 25° C., and wherein an in vivo release of lurasidone is extended over a period of great than 1 week.

2. The process of claim 1, wherein the process further comprises adding additional excipients to form a final dosage form.

3. A process for preparing a non-aqueous long acting injectable formulation, comprising:

i. mixing about 0.5% to about 10% by weight of the formulation of an amphiphilic agent selected from the group consisting of ethanol, benzyl alcohol, benzyl benzoate, N-methyl-2-pyrrolidone, dimethylacetamide, sorbitan esters, polyethoxylated sorbitan esters, fatty alcohol ethoxylates, fatty acid ethoxylates, polyoxyethylene polyoxypropylene block copolymers, and combinations thereof with about 80% to about 95% by weight of the formulation of a non-aqueous liquid vehicle comprising a hydrophobic lipid comprising a glyceryl ester of a $C_6$-$C_{24}$ fatty acid, and ii. dispersing about 5% to about 20% by weight of the formulation of lurasidone as free base or salt having a Do particle size of about 0.5 μm to about 25 μm in the mixture of (i) and mixing to form a uniform dispersion to obtain the long acting injectable formulation, wherein the long acting injectable formulation is non-gelling and thixotropic with a viscosity of less than 10 poise at a shear rate of 10/s at 25° C. and a viscosity of greater than 15 poise at a shear rate of less than or equal to about 0.1/s at 25° C., and wherein an in vivo release of lurasidone is extended over a period of greater than 1 week.

4. The process of claim 3, wherein the process further comprises adding additional excipients to form a final dosage form.

5. The process of claim 1, wherein the hydrophobic lipid is a glyceryl ester of a $C_{12}$-$C_{18}$ fatty acid.

6. The process of claim 3, wherein the hydrophobic lipid is a glyceryl ester of a $C_{12}$-$C_{18}$ fatty acid.

7. The process of claim 1, wherein the milling in (iii) is a wet milling process or a dry milling process.

8. The process of claim 7, wherein the wet milling process is ball/media milling, high shear milling or high pressure homogenizer milling.

9. The process of claim 7, wherein the dry milling process is an air jet mill.

* * * * *